United States Patent
Sheldon et al.

(10) Patent No.: US 7,927,601 B2
(45) Date of Patent: Apr. 19, 2011

(54) VARIANTS OF HEPATITIS B VIRUS WITH RESISTANCE TO ANTI-VIRAL NUCLEOSIDE AGENTS AND APPLICATIONS THEREOF

(75) Inventors: Julie Sheldon, Madrid (ES); Berta Rodes, Madrid (ES); Vincent Soriano, Madrid (ES); Angeline Ingrid Bartholomeusz, Carnegie (AU)

(73) Assignees: Melbourne Health, Parkville, Victoria (AU); Fundacion Investigacion y Educacion En Sida, Madrid (ES)

( * ) Notice: Subject to any disclaimer, the term of this patent is extended or adjusted under 35 U.S.C. 154(b) by 829 days.

(21) Appl. No.: 11/576,249

(22) PCT Filed: Sep. 28, 2005

(86) PCT No.: PCT/AU2005/001489
§ 371 (c)(1),
(2), (4) Date: Jun. 7, 2007

(87) PCT Pub. No.: WO2006/034545
PCT Pub. Date: Apr. 6, 2006

(65) Prior Publication Data
US 2010/0047281 A1 Feb. 25, 2010

(30) Foreign Application Priority Data
Sep. 28, 2004 (AU) .............................. 2004905615

(51) Int. Cl.
*C12Q 1/70* (2006.01)
*C12N 7/00* (2006.01)

(52) U.S. Cl. ... 424/189.1; 424/227.1; 435/5; 435/235.1; 435/193; 435/194

(58) Field of Classification Search .................. None
See application file for complete search history.

(56) References Cited

U.S. PATENT DOCUMENTS
2006/0051743 A1* 3/2006 Bartholomeusz et al. ........ 435/5

FOREIGN PATENT DOCUMENTS

| CA | 2309379 A1 | 12/2001 |
|---|---|---|
| WO | WO 03/066841 A1 | 8/2003 |
| WO | WO 03/087351 A1 | 10/2003 |
| WO | WO 2004/031224 A2 | 4/2004 |
| WO | WO 2005/042733 A1 | 5/2005 |

OTHER PUBLICATIONS

Bartholomeusz, S.L. et al. 2005 "Mechanistic basis for hepatitis B virus resistance to acyclic nucleoside phosphonate analogues, adefovir and tenofovir" *Hepatology* 42(4): Suppl 1, p. 594A (Abstract).
Gallant, J.E. and Deresinski, S. 2003 "Tenofovir disproxil fumarate" *Clin Infect Dis* 37(7):944-950.
GenBank Accession No. AY217375, Hepatitis B virus isolate 599, complete genome, Jul. 15, 2004. Cites Luo, K. et al. 2004 "The putative recombination of hepatitis B virus genotype B with pre-C/C region of genotype C" *Virus Genes* 29(1): 31-41. (Abstract only).
Sheldon, J. et al. 2005 "Selection of hepatitis B virus polymerase mutations in HIV-coinfected patients treated with tenofovir" *Antiviral Therapy* 10:727-734.
Torresi, J. 2002 "The virological and clinical significance of mutations in the overlapping envelope and polymerase genes of hepatitis B virus" *J Clin Virol* 25:97-106.
Walters, K-A. et al. 2003 "Generation of stable cell lines expressing lamivudine-resistant hepatitis B virus for antiviral-compound screening" *Antimicrobial Agents and Chemotherapy* 47(6):1936-1942.
Delaney IV, W.E. et al. 2006. "Intracellular metabolism and *in vitro* activity of Tenofovir against Hepatitis B virus" *Antimicrobial Agents and Chemotherapy* 50(7): 2471-2477.
Kuo, A. et al. 2004. "Tenofovir Disoproxil Fumarate for the treatment of Lamivudine-resistant Hepatitis B" *Clinical Gastroenterology and Hepatology* 2: 266-272.
Stuyver, L.J. et al. 2001. "Nomenclature for antiviral-resistant human Hepatitis B virus mutations in the polymerase region" *Hepatology* 33(3): 751-757.
Supplementary European Search Report, European Patent Application No. EP 05 79 1326, dated Jan. 18, 2008.

* cited by examiner

*Primary Examiner* — Bo Peng
(74) *Attorney, Agent, or Firm* — Knobbe Martens Olson & Bear LLP

(57) ABSTRACT

The present invention relates generally to viral variants exhibiting reduced sensitivity to particular agents and/or reduced interactivity with immunological reagents. More particularly, the present invention is directed to hepatitis B virus (HBV) variants exhibiting complete or partial resistance to nucleoside or nucleotide analogs or other antagonists of HBV DNA polymerase activity and/or reduced interactivity with antibodies to viral surface components including reduced sensitivity to these antibodies. The present invention further contemplates assays for detecting such viral variants. These assays are useful in monitoring anti-viral therapeutic regimens and in developing new or modified vaccines directed against viral agents and in particular the resistant HBV variants of the present invention. The present invention also contemplates the use of the viral variants to screen for agents capable of inhibiting infection, replication and/or release of the virus.

11 Claims, 11 Drawing Sheets

TCTAGGGGGATCACCCGTGTGTCTTGGCCAAAATTCGCAGTCCCCAACCTCCA
ATCACTCACCAACCTCCTGTCCTCCAATTTGTCCTGGTTATCGCTGGATGTGTC
TGCGGCGTTTTATCATATTCCTCTTCATCCTGCTGCTATGCCTCATCTTCTTATT
GGTTCTTCTGGATTATCAAGGTATGTTGCCCGTTTGTCCTCTAATTCCAGGATC
AACAACAACCAGTACGGGACCATGCAAAACCTGCACGACTCCTGCTCAAGGC
AACTCTATGTTTCCCTCATGTTGCTGTACAAAACCTACGGATGGAAATTGCACC
TGTATTCCCATCCCATCGTCCTGGGCTTTCGCAAATACCTATGGGAGTGGGCC
TCAGTCCGTTTCTCTTGGCTCAGTTTACTAGTGCCATTTGTTCAGTGGTTCGTAG
GGCTTTCCCCCACTGTTTGGCTTTCAGCTATATGGATGATGTGGTATTGGGGGC
CAAGTCTGTACAGCATCGTGAGTCCCTTTATACCGCTGTTACCAATTTTCTTTT
GTCTCTGGGTATACATTTAAACCCTAACAAAACAAAAAGATGGGGTTATTCCC
TAAACTTCATGGGTTACATAATTGGAAGTTGGGGAACATTGCCACAGGATCAT
ATTGTACAAAAGATCAAGCACTGTTTTAGAAAACTTCCTGTTAACAGGCCTATT
GATTGGAAAGTATGTCAAAGAATTGTGGGTCTTTTGGGCTTTGCTGCTCCATTT
A

Figure 3

SRGITRVSWPKFAVPNLQSLTNLLSSNLSWLSLDVSAAFYHIPLHPAAMPHLLIGSS
GLSRYVARLSSNSRINNNQYGTMQNLHDSCSRQLYVSLMLLYKTYGWKLHLYSH
PIVLGFRKIPMGVGLSPFLLAQFTSAICSVVRRAFPHCLAFSYMDDVVLGAKSVQH
RESLYTAVTNFLLSLGIHLNPNKTKRWGYSLNFMGYIIGSWGTLPQDHIVQKIKHC
FRKLPVNRPIDWKVCQRIVGLLGFAAPF

Figure 4

LGGSPVCLGQNSQSPTSNHSPTSCPPICPGYRWMCLRRFIIFLFILLLCLIFLLVLLDY
QGMLPVCPLIPGSTTTSTGPCKTCTTPAQGNSMFPSCCCTKPTDGNCTCIPIPSSWA
FAKYLWEWASVRFSWLSLLVPFVQWFVGLSPTVWLSAIWMMWYWGPSLYSIVS
PFIPLLPIFFCLWVYI*

Figure 5

TCTAGGGGGATCACCCGTGTGTCTTGGCCAAAATTCGCAGTCCCCAACCTCCA
ATCACTCACCAACCTCCTGTCCTCCAATTTGTCCTGGTTATCGCTGGATGTGTC
TGCGGCGTTTTATCATATTCCTCTTCATCCTGCTGCTATGCCTCATCTTCTTATT
GGTTCTTCTGGATTATCAAGGTATGTTGCCCGTTTGTCCTCTAATTCCAGGATC
AACAACAACCAGTACGGGACCATGCAAACCTGCACGACTCCTGCTCAAGGC
AACTCTATGTTTCCCTCATGTTGCTGTACAAACCTACGGATGGAAATTGCACC
TGTATTCCCATCCCATCGTCCTGGGCTTTCGCAAATACCTATGGGAGTGGGCC
TCAGTCCGTTTCTCTTGGCTCAGTTACTAGTGCCATTTGTTCAGTGGTTCGTAG
GGCTTTCCCCACTGTTTGGCTTTCAGCTATATGGATGATGTGGTATTGGGGGC
CAAGTCTGTACAGCATCGTGAGTCCCTTTATACCGCTGTTACCAATTTTCTTTT
GTCTCTGGGTATACATTTAAACCCTAACAAAACAAAAGATGGGGTTATTCCC
TAAACTTCATGGGYTACATAATTGGAAGTTGGGGAACATTGCCACAGGATCAT
ATTGTACAAAGATCAAACACTGTTTTAGAAAACTTCCTGTTAACAGGCCTATT
GATTGGAAAGTATGTCAAAGAATTGTGGGTCTTTGGGCTTTGCTGC

Figure 6

SRGITRVSWPKFAVPNLQSLTNLLSSNLSWLSLDVSAAFYHIPLHPAAMPHLLIGSS
GLSRYVARLSSNSRINNNQYGTMQNLHDSCSRQLYVSLMLLYKTYGWKLHLYSH
PIVLGFRKIPMGVGLSPFLLAQFTSAICSVVRRAFPHCLAFSYMDDVVLGAKSVQH
RESLYTAVTNFLLSLGIHLNPNKTKRWGYSLNFMGYIIGSWGTLPQDHIVQKIKHC
FRKLPVNRPIDWKVCQRIVGLLGFA

Figure 7

LGGSPVCLGQNSQSPTSNHSPTSCPPICPGYRWMCLRRFIIFLFILLLCLIFLLVLLDY
QGMLPVCPLIPGSTTTSTGPCKTCTTPAQGNSMFPSCCCTKPTDGNCTCIPIPSSWA
FAKYLWEWASVRFSWLSLLVPFVQWFVGLSPTVWLSAIWMMWYWGPSLYSIVS
PFIPLLPIFFCLWVYI

Figure 8

TCTAGGGGGATCTCCCGTGTGTCTTGGCCAAAATTCGCAGTCCCCAACCTCCAA
TCACTCACCAACCTCCTGTCCTCCAATTTGTCCTGGTTATCGCTGGATGTGTCT
GCGGCGTTTTATCATATTCCTCTTCATCCTGCTGCTATGCCTCATCTTCTTATTG
GTTCTTCTGGATTATCAAGGTATGTTGCCCGTTTGTCCTCTAATTCCAGGATCA
ACAACAACCAGTACGGGACCATGCAAAACCTGCACGACTCCTGCTCAAGGCA
ACTCTATGTTTCCCTCATGTTGCTGTACAAAACCTACGGATGGAAATTGCACCT
GTATTCCCATCCCATCGTCCTGGGCTTTCGCAAAATACCTATGGGAGTGGGCCT
CAGTCCGTTTCTCATGGCTCAGTTTACTAGTGCCATTTGTTCAGTGGTTCGTAG
GACTTTCCCCCACTGTTTGGCTTTCAGCTATGTGGATGATGTGGTATTGGGGGC
CAAGTCTGTACAGCATCGTGAGTCCCTTTATACCGCTGTTACCAATTTTCTTTT
GTCTCTGGGTATACATTTAAACCCTAACAAAACAAAAGATGGGGTTATTCCC
TAAACTTCATGGGCTACATAATTGGAAGTTGGGGAACTTTGCCACAGGATCAT
ATTGTACAAAAGATCAAACACTGTTTTAGAAAACTTCCTGTTAACAGGCCTATT
GATTGGAAAGTATGTCAAAGAATTGTGGGTCTTTTGGGCTTTGCTGCTCCATTT
ACACAATGTGGATATCCTGCCTTAATGCCTTTGTATGCATGTATACAAGCTAAA
CAGGCTTTCACTTT

Figure 9

SRGISRVSWPKFAVPNLQSLTNLLSSNLSWLSLDVSAAFYHIPLHPAAMPHLLIGSS
GLSRYVARLSSNSRINNNQYGTMQNLHDSCSRQLYVSLMLLYKTYGWKLHLYSH
PIVLGFRKIPMGVGLSPFLMAQFTSAICSVVRRTFPHCLAFSYVDDVVLGAKSVQH
RESLYTAVTNFLLSLGIHLNPNKTKRWGYSLNFMGYIIGSWGTLPQDHIVQKIKHC
FRKLPVNRPIDWKVCQRIVGLLGFAAPFTQCGYPALMPLYACIQAKQAFT

Figure 10

LGGSPVCLGQNSQSPTSNHSPTSCPPICPGYRWMCLRRFIIFLFILLLCLIFLLVLLDY
QGMLPVCPLIPGSTTTSTGPCKTCTTPAQGNSMFPSCCCTKPTDGNCTCIPIPSSWA
FAKYLWEWASVRFSWLSLLVPFVQWFVGLSPTVWLSAMWMMWYWGPSLYSIV
SPFIPLLPIFFCLWVYI

Figure 11

TCTAGGGGGATCTCCCGTGTGTCTTGGCCAAAATTCGCAGTCCCCAACCTCCAA
TCACTCACCAACCTCCTGTCCTCCAATTTGTCCTGGTTATCGCTGGATGTGTCT
GCGGCGTTTTATCATATTCCTCTTCATCCTGCTGCTATGCCTCATCTTCTTATTG
GTTCTTCTGGATTATCAAGGTATGTTGCCCGTTTGTCCTCTAATTCCAGGATCA
ACAACAACCAGTACGGGACCATGCAAAACCTGCACGACTCCTGCTCAAGGCA
ACTCTATGTTTCCCTCATGTTGCTGTACAAACCTACGGATGGAAATTGCACCT
GTATTCCCATCCCATCGTCCTGGGCTTTCGCAAAATACCTATGGGATTGGGCCT
CAGTCCGTTTCTCATGGCTCAGTTTACTAGTGCCATTTGTTCAGTGGTTCGTAG
GACTTTCCCCCACTGTTTGGCTTTTAGCTATGTGGATGATGTGGTATTGGGGGC
CAAGTCTGTACAGCATCGTGAGTCCCTTTATACCGCTGTTACCAATTTTCTTTT
GTCTCTGGGTATACATTTAAACCCTAACAAAACAAAAGATGGGGTTATTCCC
TAAACTTCATGGGTTACATAATTGGAAGTTGGGGAACATTGCCACAGGATCAT
ATTGTACAAAGATCAAACACTGTTTTAGAAAACTTCCTGT

Figure 12

SRGISRVSWPKFAVPNLQSLTNLLSSNLSWLSLDVSAAFYHIPLHPAAMPHLLIGSS
GLSRYVARLSSNSRINNNQYGTMQNLHDSCSRQLYVSLMLLYKTYGWKLHLYSH
PIVLGFRKIPMGLGLSPFLMAQFTSAICSVVRRTFPHCLAFSYVDDVVLGAKSVQH
RESLYTAVTNFLLSLGIHLNPNKTKRWGYSLNFMGYIIGSWGTLPQDHIVQKIKHC
FRKLP

Figure 13

LGGSPVCLGQNSQSPTSNHSPTSCPPICPGYRWMCLRRFIIFLFILLLCLIFLLVLLDY
QGMLPVCPLIPGSTTTSTGPCKTCTTPAQGNSMFPSCCCTKPTDGNCTCIPIPSSWA
FAKYLWDWASVRFSWLSLLVPFVQWFVGLSPTVWLLAMWMMWYWGPSLYSIV
SPFIPLLPIFFCLWVYI*

Figure 14

VARIANTS OF HEPATITIS B VIRUS WITH RESISTANCE TO ANTI-VIRAL NUCLEOSIDE AGENTS AND APPLICATIONS THEREOF

This application is U.S. National Phase of International Application PCT/AU2005/001489, filed Sep. 28, 2005, designating the U.S., and published in English as WO 2006/034545 on Apr. 6, 2006, which claims priority to Australian Patent Application No. 2004905615 filed Sep. 28, 2004.

BACKGROUND OF THE INVENTION

1. Field of the Invention

The present invention relates generally to viral variants exhibiting reduced sensitivity to particular agents and/or reduced interactivity with immunological reagents. More particularly, the present invention is directed to hepatitis B virus (HBV) variants exhibiting complete or partial resistance to nucleoside or nucleotide analogs or other antagonists of HBV DNA polymerase activity and/or reduced interactivity with antibodies to viral surface components including reduced sensitivity to these antibodies. The present invention further contemplates assays for detecting such viral variants, which assays are useful in monitoring anti-viral therapeutic regimens and in developing new or modified vaccines directed against viral agents and in particular the resistant HBV variants of the present invention. The present invention also contemplates the use of the viral variants to screen for agents capable of inhibiting infection, replication and/or release of the virus.

2. Description of the Prior Art

Bibliographic details of the publications referred to by author in this specification are collected at the end of the description.

The reference to any prior art in this specification is not, and should not be taken as, an acknowledgment or any form of suggestion that that prior art forms part of the common general knowledge in any country.

Specific mutations in an amino acid sequence are represented herein as 'Xaa$_1$nXaa$_2$' where Xaa$_1$ is the original amino acid residue before mutation, n is the residue number and Xaa$_2$ is the mutant amino acid. The abbreviation 'Xaa' may be the three letter or single letter (i.e. 'X') code. The amino acid residues for Hepatitis B virus DNA polymerase are numbered with the residue methionine in the motif Tyr Met Asp Asp (YMDD) being residue number 204 (Stuyver et al., *Hepatology* 33: 751-757, 2001). The amino acid residues for hepatitis B virus surface antigen are number according to Norder et al. (*J. Gen. Virol*. 74: 341-1348, 1993).

The term nucleoside analogs has been used in reference to both nucleotide and nucleoside analogs.

Hepatitis B virus (HBV) can cause debilitating disease conditions and can lead to acute liver failure. HBV is a DNA virus which replicates via an RNA intermediate and utilizes reverse transcription in its replication strategy (Summers and Mason, *Cell* 29: 403-415, 1982). The HBV genome is of a complex nature having a partially double-stranded DNA structure with overlapping open reading frames encoding surface, core, polymerase and X genes. The complex nature of the HBV genome is represented in FIG. 1. The polymerase consists of four functional regions, the terminal protein (TP), spacer, reverse transcriptase (rt) and ribonuclease (RNAse).

The polymerase gene of HBV overlaps the envelope gene, mutations in the catalytic domain of the polymerase can affect the amino acid sequence of the envelope protein and vice versa. In particular, the genetic sequence for the neutralization domain of HBV known as the 'a' determinant, which is found within the HBsAg and located between amino acids 99 and 169, actually overlaps the major catalytic regions of the viral polymerase protein and in particular domains A and B.

The presence of an HBV DNA polymerase has led to the proposition that nucleoside and nucleotide analogs could act as effective anti-viral agents. Examples of nucleoside analogs currently being tested are penciclovir and its oral form (FAM or FCV) [Vere Hodge, *Antiviral Chem Chemother* 4: 67-84, 1993; Boyd et al., *Antiviral Chem Chemother.* 32: 358-363, 1987; Kruger et al., *Hepatology* 22: 219A, 1994; Main et al., *J. Viral Hepatitis* 3: 211-215, 1996] Lamivudine [(−)-β-2'-deoxy-3'-thiacytidine; (3TC or LMV) [Severini et al., *Antimicrobial Agents Chemother* 39: 1430-1435, 1995; Dienstag et al., *New England J Med* 333: 1657-1661, 1995]. New nucleoside analogs which have already progressed to clinical trials include the pyriamidines Emtricitabine, ((−)-β-L-2'-3'-dideoxy-5-fluoro-3'-thiacydidine; FTC), the 5-fluoro derivative of 3TC, and Clevudine (1-(2-fluoro-5-methyl-β-L-arabino-furanosyl) uracil; L-FMAU), a thymidine analog. Like 3TC, these are pyrimidine derivatives with an unnatural "L"-configuration. Several purine derivatives have also progressed to clinical trials; they include Entecavir (BMS-200, 475; ETV), a carbocyclic deoxyguanosine analog, diaminopurine dioxolane (DAPD), an oral pro-drug for dioxolane guanine ((−)-β-D-2-aminopurine dioxolane; DXG) and Adefovir dipivoxil, an oral prodrug for the acyclic deoxyadenosine monophosphate nucleoside analog Adefovir (9-[phosphonyl-methoxyethyl]-adenine; PMEA). Tenofovir disoproxil fumarate (TDF) has activity against HBV in vitro [Lada O et al., *Antivir Ther.;* 9:353-63, 2004]. TDF has been approved for the treatment of HIV and has been used in co-infected HIV-HBV patients for the treatment of both HBV and HIV.

Whilst these agents are highly effective in inhibiting HBV DNA synthesis, there is the potential for resistant mutants of HBV to emerge during long term antiviral chemotherapy. In patients on prolonged LMV therapy key resistance mutations are selected in the rt domain within the polymerase at rtM204I/V+/−rtL180M. The nomenclature used for the polymerase mutations is in accordance with that proposed by Stuyver et al., 2001, supra. Only LMV and ADV have been approved for use against chronic HBV infection. LMV and ADV are both potent inhibitors of HBV replication and reduce HBV DNA viral load. Unfortunately, both LMV-resistant and ADV-resistant strains of HBV are selected during therapy.

HIV and HBV are both blood borne viruses and have similar potential routes of transmission. Approximately 10% of HIV infected individuals are co-infected with HBV. The improved prognosis of HIV-infection that has occurred since the introduction of highly active antiretroviral therapy (HAART) has resulted in renewed emphasis being placed on co-morbidities associated with HIV-infection, and chronic viral hepatitis in particular. Hepatitis B virus (HBV) infection is an important infection in HIV-1 infected individuals because of the influence of HIV-1 co-infection on the natural history of HBV infection. Antiviral therapies with activity against both viruses have enabled targeted therapy in co-infected individuals. However, antiviral resistance is an important issue for both HIV and HBV.

TDF is also a potent inhibitor of HBV replication. TDF has activity against both hepadnaviruses and HIV. TDF was formerly referred to as bis-POC PMPA the oral derivative of 9-[(R)-2-(phosphonomethoxy)propyl]adenine (PMPA) [Shaw J P et al., *Pharm Res.* 14(12):1824-9, 1997]. Preclinical studies demonstrate that TDF is a highly potent inhibitor of HBV in vitro and is effective against the LMV resistant viruses [Ying C et al., *J Viral Hepat*. 7(2):161-5, 2000]. TDF has been used successfully to treat patients with the LMV resistant HBV mutations. No specific TDF resistant mutations had been described for HBV.

Nucleoside or nucleotide analog therapy may be administered as monotherapy or combination therapy where two or more nucleoside or nucleotide analogs may be administered. There is a need to monitor for development of nucleoside-/nucleotide-resistant variants of HBV as well as variants resistant to other HBV DNA polymerase antagonists and variants resistant to antibodies to HBV surface components. The rapid identification can lead to altered therapeutic protocols being pursued. In addition, resistant HBV variants are useful as targets for screening of new antiviral agents.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1, <400>2, etc. A sequence listing is provided after the claims.

The positions of nucleotide and amino acid mutations identified using nomenclature from genotypes B, C or F where the methionine residue in the YMDD motif of the DNA polymerase was designated position 550 (see Australian Patent No. 734831). The nucleotide and amino acid positions given in the present specification are based on a new nomenclature where the methionine residue is YMDD is position 204 and is referred to as rtM204 where rt is an abbreviation for "reverse transcriptase".

In accordance with the present invention, HBV resistant variants were identified in two patients (patient A and patient B) with chronic hepatitis B and HIV, treated with both LMV and TDF. In combination therapy, accordance with the present invention, resistant variants of HBV were identified, following LMV and TDF treatment, with mutations in the HBV DNA polymerase gene which reduce the sensitivity of HBV to nucleoside and nucleotide analogs. The identification of these HBV variants is important for the development of assays to monitor LMV and/or TDF resistance and/or resistance to other nucleoside or nucleotide analog therapeutic regimes and to screen for agents which are useful as alternative therapeutic agents. The mutations detected in the HBV isolated from patients A and B were the LMV resistant mutations namely the rtV173L+rtL180M+rtM204V in association with a unique mutation at rtA194T.

The detection of such HBV variants is particularly important in the management of therapeutic protocols including the selection of appropriate agents for treating HBV infection. The method of this aspect of the present invention is predicated in part on monitoring the development in a subject of an increased HBV load in the presence of a nucleoside or nucleotide analog and/or the presence of antibodies to viral surface components. The clinician is then able to modify an existing treatment protocol or select an alternative treatment protocol accordingly. In addition, the present invention encompasses HBV variants obtained from subjects following exposure to LMV and/or TDF but which are still sensitive to one or both of LMV and/or TDF. Such variants may exhibit resistance to other nucleoside or nucleotide analogs and/or to antibodies to viral surface components.

One aspect of the present invention, therefore, is directed to an isolated HBV variant comprising a nucleotide mutation in a gene encoding a DNA polymerase resulting in at least one amino acid addition, substitution and/or deletion to the DNA polymerase and which exhibits decreased sensitivity to TDF and/or LMV and optionally, in addition or alternatively, other nucleoside or nucleotide analogs, other HBV DNA polymerase antagonists and/or or immunological reagents. In this regard, exposure of a patient to TDF and/or LMV may result in the selection of an HBV variant which exhibits resistance or reduced sensitivity to a nucleoside or nucleotide analog other than TDF or LMV or to an immunology reagent such as an antibody to an HBV surface antigen. Preferably, the DNA polymerase exhibits reduced sensitivity to TDF, or and LMV. The variant HBV comprises a mutation in an overlapping open reading frame in its genome in a region defined by one or more of domains F and A through E of HBV DNA polymerase.

The present invention further contemplates a method for determining the potential for an HBV to exhibit reduced sensitivity to TDF and/or LMV or optionally, in addition or alternatively, other nucleoside or nucleotide analogs, other HBV DNA polymerase antagonists and/or immunological reagents by isolating DNA or corresponding mRNA from the HBV and screening for a mutation in the nucleotide sequence encoding HBV DNA polymerase resulting in at least one amino acid substitution, deletion and/or addition in any one or more of domains F and A through E or a region proximal thereto of the DNA polymerase and associated with resistance or decreased sensitivity to TDF and/or LMV. The presence of such a mutation is an indication of the likelihood of resistance to said entecavir and/or LMV. Preferably, the HBV variant exhibits reduced sensitivity to TDF, or both TDF and LMV.

The present invention also provides a composition comprising a variant HBV resistant to TDF and/or LMV and optionally, in addition or alternatively, other nucleoside or nucleotide analogs, other HBV DNA polymerase antagonists and/or immunological reagents or a recombinant or derivative form thereof or its chemical equivalent and one or more pharmaceutically acceptable carriers and/or diluents. Yet another aspect of the present invention provides a use of the aforementioned composition or a variant HBV comprising a nucleotide mutation in a gene encoding a DNA polymerase resulting in at least one amino acid addition, substitution and/or deletion to the DNA polymerase and a decreased sensitivity to TDF and/or LMV and optionally in addition or alternatively other nucleoside or nucleotide analogs or other HBV DNA polymerase antagonists or immunological reagents in the manufacture of a medicament for the treatment and/or prophylaxis of HBV infection.

The present invention also contemplates a method for determining whether an HBV strain exhibits reduced sensitivity to a nucleoside or nucleotide analog, or other HBV DNA polymerase antagonist by isolating DNA or corresponding mRNA from the HBV and screening for a mutation in the nucleotide sequence encoding the DNA polymerase wherein the presence of the following mutations in the rt region: rtV173L, rtL180M, rtA194T and rtM204V or combinations thereof or an equivalent one or more other mutation is indicative of a variant which exhibits a decreased sensitivity to TDF and/or LMV and optionally other nucleoside or nucleotide analogs and/or other HBV DNA polymerase antagonists and/or an immunological reagent.

The subject method may also be practiced by screening for a mutation in the nucleotide sequence encoding the DNA polymerase wherein the presence of the following mutations in the B or C domain of the rt region: rtV173L, rtL180M, rtA194T and rt M204V or combinations thereof or an equivalent one or more other mutations is indicative of a variant which exhibits a decreased sensitivity to TDF and/or LMV and optionally other nucleoside or nucleotide analogs, or other HBV DNA polymerase antagonists and/or an immunological reagent.

It should be noted that mutants, rtV173L, rtL180M and rtM204V correspond to mutants, V519L, L526M, and M550V, respectively in Australian Patent No. 734831 (using an earlier nomenclature system).

Still a further methodology comprises screening for a mutation in the nucleotide sequence encoding the envelope genes wherein the presence of the following mutations in the PreS1, PreS2 and S genes (changes in the overlapping reverse transcriptase region are indicated in parenthesis): sE164D (=rtV173L), sS193L (no change), sI195M (=rtM204V), combinations thereof or an equivalent one or more other mutation is indicative of a variant which exhibits a decreased sensitivity to TDF and/or LMV and optionally other nucleoside or nucleotide analogs, or other HBV DNA polymerase antagonists and/or an immunological reagent.

Another aspect of the present invention is directed to a variant HBV comprising a surface antigen having an amino acid sequence with a single or multiple amino acid substitution, addition and/or deletion or a truncation compared to a surface antigen from a reference or wild type HBV and wherein an antibody generated to the reference or wild type surface antigen exhibits an altered immunological profile relative to said HBV variant. One altered profile includes a reduced capacity for neutralizing the HBV. More particularly, the surface antigen of the variant HBV exhibits an altered immunological profile compared to a pre-treatment HBV where the variant HBV is selected for by a nucleoside or nucleotide analog or other antagonist of the HBV DNA polymerase. The variant HBV of this aspect of the invention may also comprise a nucleotide sequence comprising a single or multiple nucleotide substitution, addition and/or deletion compared to a pre-treatment HBV.

The present invention extends to an isolated HBsAg or a recombinant form thereof or derivative or chemical equivalent thereof corresponding to the variant HBV. Generally, the HBsAg or its recombinant or derivative form or its chemical equivalent comprises an amino acid sequence with a single or multiple amino acid substitution, addition and/or deletion or a truncation compared to an HBsAg from a reference HBV and wherein an antibody directed to a reference HBV exhibits an altered immunological profile to an HBV carrying said variant HBsAg. In one embodiment, the altered immunological profile comprises a reduction in the ability to neutralize the variant HBV.

The present invention is predicated in part on the identification and isolation of variants of HBV that have a plurality of mutations and exhibit two or more characteristics selected from decreased or reduced sensitivity to one or more nucleoside or nucleotide analogs or other HBV DNA polymerase antagonist, a reduced level and/or functional activity of Hepatitis Be antigen, or a reduced, abrogated or otherwise impaired immunological interactivity, relative to wild-type HBV. Thus, the identification of HBV variants with these mutational patterns is important inter alia for the development of assays to detect HBV variants and assays to screen for agents which are useful in treating and/or preventing infections by those variants and/or other HBV isolates and for the development of alternative therapeutic regimes for managing HBV infections.

Accordingly, one aspect of the present invention is directed to an isolated HBV variant comprising a plurality of nucleotide mutations that correlate with at least two characteristics selected from (a) resistance to one or more nucleoside analogs, (b) a reduced level and/or functional activity of Hepatitis Be antigen, or (c) a reduced, abrogated or otherwise impaired immunological interactivity.

Another aspect of the present invention contemplates an isolated HBV variant comprising a plurality of nucleotide mutations that correlate with (a) resistance to one or more nucleoside or nucleotide analogs or other antagonists of HBV DNA polymerase activity, (b) a reduced level and/or functional activity of Hepatitis Be antigen, and (c) a reduced, abrogated or otherwise impaired immunological interactivity.

Yet another aspect of the present invention provides an isolated HBV variant comprising a plurality of nucleotide mutations selected from two or more of (a) a nucleotide mutation in a gene encoding a DNA polymerase resulting in at least one amino acid addition, substitution and/or deletion to said DNA polymerase wherein said variant exhibits decreased sensitivity to TDF and/or LMV and optionally other nucleoside or nucleotide analogs or other antagonists of HBV DNA polymerase activity, (b) a nucleotide mutation in a gene encoding a Hepatitis Be antigen or in a transcriptional control element of said gene wherein said mutation results in a reduced level and/or functional activity of said Hepatitis Be antigen, or (c) a nucleotide mutation in a gene encoding a hepatitis B polypeptide resulting in at least one amino acid addition, substitution and/or deletion to said polypeptide which reduces, abrogates or otherwise impairs its immunological interactivity.

Another aspect of the present invention contemplates a method for detecting an agent which exhibits inhibitory activity to an HBV by generating a genetic construct comprising a replication competent-effective amount of the genome from the HBV contained in a plasmid vector and then transfecting said cells with said construct, contacting the cells, before, during and/or after transfection, with the agent to be tested, culturing the cells for a time and under conditions sufficient for the HBV to replicate, express genetic sequences and/or assemble and/or release virus or virus-like particles if resistant to said agents; and the subjecting the cells, cell lysates or culture supernatant fluid to viral- or viral-component-detection means to determine whether or not the virus has replicated, expressed genetic material and/or assembled and/or been released in the presence of the agent. In a preferred embodiment, the plasmid vector in a baculovirus vector and the method comprises generating a genetic construct comprising a replication competent-effective amount of the genome from the HBV contained in or fused to an amount of a baculovirus genome effective to infect cells and then infecting said cells with said construct, contacting the cells, before, during and/or after infection, with the agent to be tested, culturing the cells for a time and under conditions sufficient for the HBV to replicate, express genetic sequences and/or assemble and/or release virus or virus-like particles if resistant to said agent and then subjecting the cells, cell lysates or culture supernatant fluid to viral- or viral-component-detection means to determine whether or not the virus has replicated, expressed genetic material and/or assembled and/or been released in the presence of the agent.

In an alternative embodiment, the method comprises generating a continuous cell line comprising an infectious copy of the genome of the HBV in a replication competent effective amount such that said infectious HBV genome is stably integrated into said continuous cell line such as but not limited to 2.2.15 or AD, contacting the cells with the agent to be tested, culturing the cells for a time and under conditions sufficient for the HBV to replicate, express genetic sequences and/or assemble and/or release virus or virus-like particles if resistant to the agent and then subjecting the cells, cell lysates or culture supernatant fluid to viral- or viral-component-detection means to determine whether or not the virus has replicated, expressed genetic material and/or assembled and/or been released in the presence of the agent.

In an alternative embodiment, the present invention also contemplate a method for detecting an agent which exhibits inhibitory activity to an HBV polymerase in an in vitro polymerase assay. The HBV polymerase activity can be examined using established assays (Gaillard et al., *Antimicrob Agents Chemother.* 46(4): 1005-1013, 2002; Xiong et al., *Hepatology.* 28(6): 1669-73, 1998). The HBV polymerase may be a wild-type or reference HBV polymerase or mutant HBV polymerase.

In connection with these methods, the plasmid vector may include genes encoding part or all of other viral vectors such as baculovirus vectors or adenovirus vectors (see Ren and Nassal, *J. Virol.* 75(3): 1104-1116, 2001).

The identification of viral variants enables the production of vaccines comprising particular recombinant viral components such as polymerases or envelope genes PreS1, PreS2, S encoding for L, M, S proteins as well as therapeutic vaccines comprising defective HBV variants. Rational drug design may also be employed to identify or generate therapeutic molecules capable of interacting with a polymerase or envelope genes PreS1, PreS2, S encoding for L, M, S proteins or other component of the HBV. Such drugs may also have diagnostic potential.

The abbreviations defined in Table 1 are used in the subject specification

TABLE 1

Abbreviations

| ABBREVIATION | DESCRIPTION |
| --- | --- |
| 3TC | (LMV); (−)-β-2'-deoxy-3'-thiacytidine |
| ADV | Adefovir |
| DAPD | diaminopurine dioxolane |
| DDI | Didanosine |
| DXG | dioxolane guanine |
| ETV | Entecavir |
| FAM | Famciclovir |
| FTC | Emtricitabine |
| HBsAg | hepatitis B surface antigen |
| HBV | hepatitis B virus |
| HIV | human immunodeficiency virus |
| LMV | Lamividuine |
| LPV/r | Lopinavir/ritonavir |
| nt | nucleotide |
| PMEA | Adefovir |
| PMPA | 9-[(R)-2-(phosphonomethoxy)propyl]adenine |
| RNAse | Ribonuclease |
| rt | reverse transcriptase |
| TDF | Tenofovir disoproxil fumarate |
| YMDD | Tyr Met Asp Asp-a motif in the polymerase protein; where the Met residue is designated residue number 204 of the reverse transcriptase |

A summary of sequence identifiers used throughout the subject specification is provided in Table 2.

TABLE 2

Summary of sequence identifiers

| SEQUENCE ID NO: | DESCRIPTION |
| --- | --- |
| 1 | primer 1 forward |
| 2 | primer 2 forward |
| 3 | primer 3 reverse |
| 4 | primer 4 reverse |
| 5 | Patient A HBV nucleotide (nt) sequence encoding catalytic region of DNA polymerase Week 0 (FIG. 3) |
| 6 | Patient A HBV amino acid sequence of catalytic region of DNA polymerase Week 0 (FIG. 4) |
| 7 | Patient A HBV amino acid sequence of surface antigen (HBsAg) Week 0 (FIG. 5) |
| 8 | Patient A HBV nt sequence of encoding catalytic region of DNA polymerase Week 48 (FIG. 6) |
| 9 | Patient A HBV amino acid sequence of catalytic region of DNA polymerase gene Week 48 (FIG. 7) |
| 10 | Patient A HBV amino acid sequence of surface antigen (HBsAg) Week 48 (FIG. 8) |
| 11 | Patient A HBV nt sequence of encoding catalytic region of DNA polymerase Week 62 (FIG. 9) |
| 12 | Patient A HBV amino acid sequence of catalytic region of DNA polymerase gene Week 62 (FIG. 10) |
| 13 | Patient A HBV amino acid sequence of surface antigen (HBsAg) Week 62 (FIG. 11) |
| 14 | Patient B HBV nt sequence of encoding catalytic region of DNA polymerase Week 77 (FIG. 12) |
| 15 | Patient B HBV amino acid sequence of catalytic region of DNA polymerase gene Week 77 (FIG. 13) |
| 16 | Patient B HBV amino acid sequence of surface antigen (HbsAg) Week 77 (FIG. 14) |
| 17 | rtM204V forward primer |
| 18 | rtM204V reverse primer |
| 19 | rt180 forward primer |
| 20 | rt180 reverse primer |
| 21 | A194T forward primer |
| 22 | A194T reverse primer |
| 23 | 3FL-XHybprobe probe |
| 24 | 5LC-XHybprobe probe |
| 25 | X sense probe |
| 26 | X antisense probe |

BRIEF DESCRIPTION OF THE FIGURES

FIG. 3 is a representation showing the HBV nucleotide sequence (SEQ ID NO: 5) encoding the catalytic region of the polymerase gene from Patient A at week 0 of TDF treatment.

FIG. 4 is a representation showing the deduced amino acid sequence (SEQ ID NO: 6) of the catalytic region of the polymerase gene from Patient A at week 0 of TDF treatment.

FIG. 5 is a representation showing the deduced amino acid sequence (SEQ ID NO: 7) of the envelope gene from Patient A week 0 of TDF treatment.

FIG. 6 is a representation showing the HBV nucleotide sequence (SEQ ID NO: 8) encoding the catalytic region of the polymerase gene from Patient A at week 48 of TDF treatment.

FIG. 7 is a representation showing the deduced amino acid sequence (SEQ ID NO: 9) of the catalytic region of the polymerase gene from Patient A at week 48 of TDF treatment.

FIG. 8 is a representation showing the deduced amino acid sequence (SEQ ID NO: 10) of the envelope gene from Patient A week 48 of TDF treatment.

FIG. 9 is a representation showing the HBV nucleotide sequence (SEQ ID NO: 11) encoding the catalytic region of the polymerase gene from Patient A at week 62 of TDF treatment.

FIG. 10 is a representation showing the deduced amino acid sequence (SEQ ID NO: 12) of the catalytic region of the polymerase gene from Patient A at week 62 of TDF treatment.

FIG. 11 is a representation showing the deduced amino acid sequence (SEQ ID NO: 13) of the envelope gene from Patient A week 62 of TDF treatment.

FIG. 12 is a representation showing the HBV nucleotide sequence (SEQ ID NO: 14) encoding the catalytic region of the polymerase gene from Patient B at week 77 of TDF treatment.

FIG. 13 is a representation showing the deduced amino acid sequence (SEQ ID NO: 15) of the catalytic region of the polymerase gene from Patient B at week 77 of TDF treatment.

FIG. 14 is a representation showing the deduced amino acid sequence (SEQ ID NO: 16) of the envelope gene from Patient B week 77 of TDF treatment.

DETAILED DESCRIPTION OF THE PRESENT INVENTION

Figure 1:
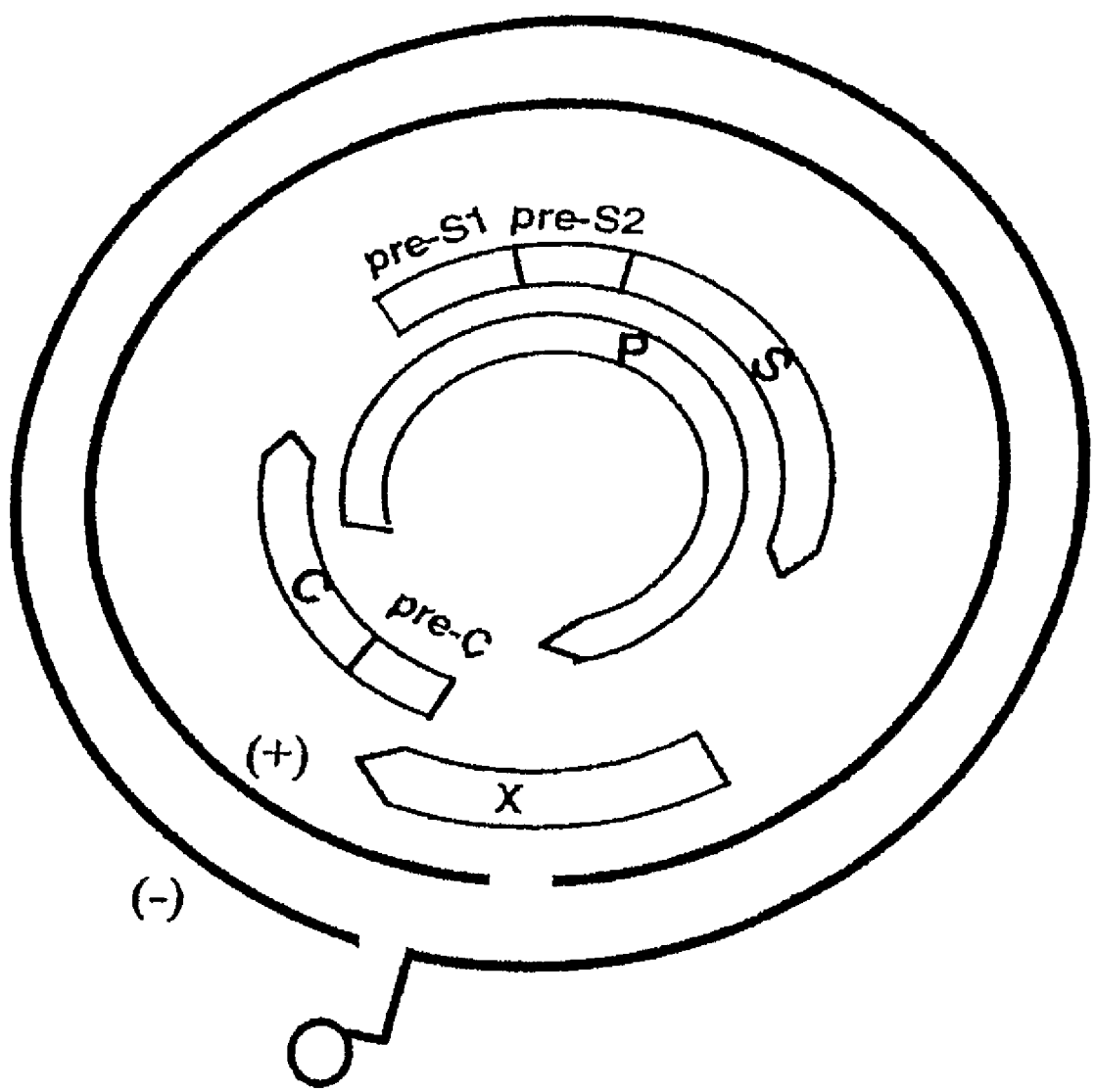
FIG. 1 is a diagrammatic representation showing the partially double stranded DNA HBV genome showing the overlapping open reading frames encoding surface (S), core (C), polymerase (P) and X gene.

The present invention is predicated in part on the identification and isolation of nucleoside or nucleotide analog resistant variants of HBV or variants resistant to other DNA polymerase antagonists or immunological reagents which bind to a surface compound of HBV following treatment of patients with TDF or LMV or TDF and LMV and optionally other nucleoside or nucleotide analogs. In particular, TDF, or TDF and LMV treated patients gave rise to variants of HBV exhibiting decreased or reduced sensitivity to TDF and/or LMV. Reference herein to "decreased" or "reduced" in relation to sensitivity to TDF and/or LMV includes and encompasses a complete or substantial resistance to the nucleoside or nucleotide analog as well as partial resistance and includes a replication rate or replication efficiency (yield phenotype) which is more than a wild-type in the presence of a nucleoside or nucleotide analog or other DNA polymerase antagonist. In one aspect, this is conveniently measured by an increase in viral load to a level similar or greater than pre-treatment levels.

Accordingly, one aspect of the present invention is directed to an isolated HBV variant wherein said variant comprises a nucleotide mutation in a gene encoding a DNA polymerase resulting in at least one amino acid addition, substitution and/or deletion to said DNA polymerase and wherein said variant exhibits decreased sensitivity to TDF and/or LMV and optionally other nucleoside or nucleotide analogs, or other HBV DNA polymerase antagonists and/or an immunological reagent.

In a related aspect, the present invention provides an isolated Hepatitis B virus (HBV) variant wherein said variant comprises a nucleotide mutation in a gene encoding a DNA polymerase resulting in at least one amino acid addition, substitution and/or deletion to said DNA polymerase and wherein said variant either exhibits decreased sensitivity to one or more of TDF and/or LMV or is selected following exposure to one or both of TDF and/or LMV.

Preferably, the decreased sensitivity is in respect of TDF, or both TDF and LMV. Alternatively or in addition, the decreased sensitivity is in respect of a nucleoside or nucleotide analog other than TDF or LMV and/or may be in respective of an immunological reagent such as an antibody to a surface compound of HBV.

In addition to a mutation in the gene encoding DNA polymerase, due to the overlapping nature of the HBV genome (FIG. 1), a corresponding mutation may also occur in the gene encoding the surface antigen (HBsAg) resulting in reduced interactivity of immunological reagents such as antibodies and immune cells to HBsAg. The reduction in the interactivity of immunological reagents to a viral surface component generally includes the absence of immunological memory to recognise or substantially recognize the viral surface component. The present invention extends, therefore, to an HBV variant exhibiting decreased sensitivity to TDF and/or LMV and reduced interactivity of an immunological reagent to HBsAg wherein the variant is selected for following TDF and/or LMV combination or sequential treatment. The term "sequential" in this respect means TDF followed by LMV or LMV followed by TDF or multiple sequential administrations of each of TDF and LMV or LMV and TDF.

A viral variant may, therefore, carry mutation only in the DNA polymerase or both in the DNA polymerase and the HBsAg. The term "mutation" is to be read in its broadest context and includes multiple mutations.

The present invention extends to a mutation and any domain of the HBV DNA polymerase and in particular regions F and A through E provided said mutation leads to decreased sensitivity to LMV and/or TDF.

Preferably, the mutation results in an altered amino acid sequence in any one or more of domains F and A through E or regions proximal thereto of the HBV DNA polymerase.

Another aspect of the present invention provides an HBV variant comprising a mutation in an overlapping open reading frame in its genome wherein said mutation is in a region defined by one or more of domains F and A through E of HBV DNA polymerase and wherein said variant exhibits decreased sensitivity to TDF and/or LMV and optionally other nucleoside or nucleotide analogs, or other HBV DNA polymerase antagonists and/or an immunological reagent.

In a related embodiment, there is provided an HBV variant comprising a mutation in the nucleotide sequence encoding a DNA polymerase resulting in an amino acid addition, substitution and/or deletion in said DNA polymerase in one or more amino acids and wherein said variant exhibits decreased sensitivity to TDF and/or LTV and optionally other nucleoside or nucleotide analogs, or other HBV DNA polymerase antagonists and/or an immunological reagent. Preferably, the decreased sensitivity is to TDF, or both LMV and/or TDF.

The term "combination therapy" means that both TDF and LMV are co-administered in the same composition or simultaneously in separate compositions. The term "sequential therapy" means that the two agents are administered within seconds, minutes, hours, days or weeks of each other and in either order. Sequential therapy also encompasses completing a therapeutic course with one or other of TDF or LMV and then completing a second therapeutic course with the other of TDF or LMV.

Accordingly, another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said the variant HBV is selected for by a nucleoside or nucleotide analog of the HBV DNA polymerase or other antagonist of the DNA polymerase, said variant selected by exposure of a subject to TDF and/or LMV in combination or sequential therapy.

In a related embodiment, the present invention provides an HBV variant comprising a nucleotide sequence comprising a single or multiple nucleotide substitution, addition and/or deletion compared to the pretreatment HBV and which HBV variant has a surface antigen exhibiting an altered immunological profile compared to the pretreatment HBV, said variant selected by exposure of a subject to TDF and/or LMV in combination or sequential therapy.

Preferably, the variants are in isolated form such that they have undergone at least one purification step away from naturally occurring body fluid. Alternatively, the variants may be maintained in isolated body fluid or may be in DNA form. The present invention also contemplates infectious molecular clones comprising the genome or parts thereof from a variant HBV. Furthermore, the present invention provides isolated components from the variant HBVs such as but not limited to an isolated HBsAg. Accordingly, the present invention provides an isolated HBsAg or a recombinant form thereof or derivative or chemical equivalent thereof, said HBsAg being from a variant HBV selected by exposure of a subject to TDF and/or LMV in combination or sequential therapy.

More particularly, yet another aspect of the present invention is directed to an isolated variant HBsAg or a recombinant or derivative form thereof or a chemical equivalent thereof wherein said HBsAg or its recombinant or derivative form or its chemical equivalent exhibits an altered immunological profile compared to an HBsAg from a reference HBV, said HBsAg being from a variant HBV selected by exposure of a subject to TDF and/or LMV in combination or sequential therapy.

Even more particularly, the present invention provides an isolated variant HBsAg or a recombinant or derivative form thereof or a chemical equivalent thereof wherein said HBsAg or its recombinant or derivative form or its chemical equivalent comprises an amino acid sequence with a single or multiple amino acid substitution, addition and/or deletion or a truncation compared to an HBsAg from a reference HBV and wherein a neutralising antibody directed to a reference HBV exhibits no or reduced neutralising activity to an HBV carrying said variant HBsAg, said HBsAg being from a variant HBV selected by exposure of a subject to TDF and/or LMV in combination or sequential therapy.

Preferred mutations in the HBV DNA polymerase include variants selected from patients with HBV recurrence following TDF and/or LMV treatment. Preferably, the treatment involves TDF or both TDF and/or LMV in combination or sequential therapy. Nucleoside or nucleotide analog treatment or other DNA polymerase antagonist treatment may occur in relation to the treatment of patients diagnosed with hepatitis in patients with HBV alone or with HBV/HIV co-infection. Following selection of variants, viral loads are obtainable at levels greater than pre-treatment levels.

Preferred mutations in the HBV DNA polymerase include one or more of rtV173L, rtL180M, rtA194T, rtM204V, or combinations thereof or an equivalent one or more other mutation is indicative of a variant wherein said variant exhibits a decreased sensitivity to TDF and/or LMV and optionally other nucleoside or nucleotide analogs, or other HBV DNA polymerase antagonists and/or an immunological reagent. It should be noted that the nomenclature system for amino acid positions is based on the methionine residues in the YMDD motif being designated codon rtM204. This numbering system is different to that in Australian Patent No. 734831 where the methionine residue in the YMDD motif within the polymerase gene is designated codon 550. In this regard, rtV173L, rtL180M and rtM204V correspond to V519L, L526M and M550V, respectively, in Australian Patent No. 734831. Corresponding mutations may also occur in envelope genes such as in one or more of PreS1, PreS2 and HBsAg. Particular mutations are as follows: sE164D, sS193L, sI195M, or combinations thereof or an equivalent one or more other mutation is indicative of a variant wherein said variant exhibits a decreased sensitivity to TDF and/or LMV and optionally other nucleoside or nucleotide analogs, or other HBV DNA polymerase antagonists and/or an immunological reagent. The mutations in gene encoding HBsAg at sE164D, or sI195M also result in mutation in the in the polymerase gene rtV173L, or rtM204V respectively.

The identification of the variants of the present invention permits the generation of a range of assays to detect such variants. The detection of such variants may be important in identifying resistant variants to determine the appropriate form of chemotherapy.

Still another aspect of the present invention contemplates a method for determining the potential for an HBV to exhibit reduced sensitivity to TDF and/or LMV or optionally other nucleoside or nucleotide analogs, or other HBV DNA polymerase antagonists and/or an immunological reagent, said method comprising isolating DNA or corresponding mRNA from said HBV and screening for a mutation in the nucleotide sequence encoding HBV DNA polymerase resulting in at least one amino acid substitution, deletion and/or addition in any one or more of domains F and A through E or a region proximal thereto of said DNA polymerase and associated with resistance or decreased sensitivity to TDF and/or LMV wherein the presence of such a mutation is an indication of the likelihood of resistance to said TDF and/or LMV.

Preferably, the assay detects one or more of the following mutations in the rt region: rtV173L, rtL180M, rtA194T, rtM204V, or combinations thereof or an equivalent one or more other mutation is indicative of a variant wherein said variant exhibits a decreased sensitivity to TDF and/or LMV and optionally other nucleoside or nucleotide analogs, or other HBV DNA polymerase antagonists and/or an immunological reagent.

Accordingly, another aspect of the present invention produces a method for determining whether an HBV strain exhibits reduced sensitivity to a nucleoside or nucleotide analogs, or other HBV DNA polymerase antagonists and/or an immunological reagent, said method comprising isolating DNA or corresponding mRNA from said HBV and screening for a mutation in the nucleotide sequence encoding the DNA polymerase wherein the presence of the following mutations in the rt region: rtV173L, rtL180M, rtA194T, rtM204V, or combinations thereof or an equivalent one or more other mutation is indicative of a variant wherein said variant exhibits a decreased sensitivity to TDF and/or LMV and optionally other nucleoside or nucleotide analogs.

In a related embodiment, the present invention contemplates a method for a method for determining the potential for an HBV to exhibit reduced sensitivity to a nucleoside or nucleotide analog selected from TDF and LMV or optionally other nucleoside or nucleotide analogs or an immunological agent, said method comprising isolating DNA or corresponding mRNA from said HBV and screening for a mutation in the nucleotide sequence encoding HBV DNA polymerase resulting in at least one amino acid substitution, deletion and/or addition in any one or more of domains F and A through E or a region proximal thereto of said DNA polymerase and associated with resistance or decreases sensitivity to one or more of TDF and/or LMV and/or an immunological agent wherein the presence of such a mutation is an indication of the likelihood of resistance to said one or more of TDF, LMV or an immunological reagent.

The preferred mutation in the reverse transcriptase is at rtA194T or combinations thereof or an equivalent one or more other mutation is indicative of a variant wherein said variant exhibits a decreased sensitivity to TDF and/or LMV and optionally other nucleoside or nucleotide analogs, or other HBV DNA polymerase antagonists and/or an immunological reagent.

Accordingly, another aspect of the present invention contemplates a method for determining whether an HBV strain exhibits reduced sensitivity to a nucleoside or nucleotide analogs, or other HBV DNA polymerase antagonists and/or an immunological reagent, said method comprising isolating DNA or corresponding mRNA from said HBV and screening for a mutation in the nucleotide sequence encoding the DNA polymerase wherein the presence of the following mutations in the B or C domain, or the B/C interdomain of the rt region:, rtV173L, rtL180M, rtA194T, rtM204V or combinations thereof or an equivalent one or more other mutation is indicative of a variant wherein said variant exhibits a decreased sensitivity to TDF and/or LMV and optionally other nucleoside or nucleotide analogs, or other HBV DNA polymerase antagonists and/or an immunological reagent.

The detection of HBV or its components in cells, cell lysates, cultured supernatant fluid and bodily fluid may be by any convenient means including any nucleic acid-based detection means, for example, by nucleic acid hybridization techniques or via one or more polymerase chain reactions (PCRs). The term "bodily fluid" includes any fluid derived from the blood, lymph, tissue or organ systems including serum, whole blood, biopsy and biopsy fluid, organ explants and organ suspension such as liver suspensions. The invention further encompasses the use of different assay formats of said nucleic acid-based detection means, including restriction fragment length polymorphism (RFLP), amplified fragment length polymorphism (AFLP), single-strand chain polymorphism (SSCP), amplification and mismatch detection (AMD), interspersed repetitive sequence polymerase chain reaction (IRS-PCR), inverse polymerase chain reaction (iPCR) and reverse transcription polymerase chain reaction (RT-PCR), amongst others. Other forms of detection include Northern blots, Southern blots, PCR sequencing, antibody procedures such as ELISA, Western blot and immunohistochemistry. A particularly useful assay includes the reagents and components required for immobilized oligonucleotide- or oligopeptide-mediated detection systems.

One particularly useful nucleic acid detection system is the reverse hybridization technique. In this technique, DNA from an HBV sample is amplified using a biotin or other ligand-labeled primer to generate a labeled amplificon. Oligonucleotides immobilized to a solid support such as a nitrocellulose film are then used to capture amplified DNA by hybridization. Specific nucleic acid fragments are identified via biotin or the ligand. Generally, the labeled primer is specific for a particular nucleotide variation to be detected. Amplification occurs only if the variation to be detected is present. There are many forms of the reverse hybridization assay and all are encompassed by the present invention.

Detecting HBV replication in cell culture is particularly useful.

Another aspect of the present invention contemplates a method for detecting an agent which exhibits inhibitory activity to an HBV by:

generating a genetic construct comprising a replication competent-effective amount of the genome from the HBV contained in a plasmid vector and then transfecting said cells with said construct;
contacting the cells, before, during and/or after transfection, with the agent to be tested;
culturing the cells for a time and under conditions sufficient for the HBV to replicate, express genetic sequences and/or assemble and/or release virus or virus-like particles if resistant to said agents; and
then subjecting the cells, cell lysates or culture supernatant fluid to viral- or viral-component-detection means to determine whether or not the virus has replicated, expressed genetic material and/or assembled and/or been released in the presence of the agent.

In a preferred embodiment, the plasmid vector may include genes encoding part or all of other viral vectors such as baculovirus or adenovirus (Ren and Nassal, 2001, supra) and the method comprises:

generating a genetic construct comprising a replication competent-effective amount of the genome from the HBV contained in or fused to an amount of a baculovirus genome or adenovirus genome effective to infect cells and then infecting said cells with said construct;
contacting the cells, before, during and/or after infection, with the agent to be tested;
culturing the cells for a time and under conditions sufficient for the HBV to replicate, express genetic sequences and/or assemble and/or release virus or virus-like particles if resistant to said agent; and
then subjecting the cells, cell lysates or culture supernatant fluid to viral- or viral-component-detection means to determine whether or not the virus has replicated, expressed genetic material and/or assembled and/or been released in the presence of the agent.

In an alternative embodiment, the method comprises:
generating a continuous cell line comprising an infectious copy of the genome of the HBV in a replication competent effective amount such that said infectious HBV genome is stably integrated into said continuous cell line such as but not limited to 2.2.15 or AD;
contacting the cells with the agent to be tested;
culturing the cells for a time and under conditions sufficient for the HBV to replicate, express genetic sequences and/or assemble and/or release virus or virus-like particles if resistant to the agent; and
then subjecting the cells, cell lysates or culture supernatant fluid to viral- or viral-component-detection means to determine whether or not the virus has replicated, expressed genetic material and/or assembled and/or been released in the presence of the agent.

As indicated above, variants may also be detected with reference to the HBsAg (s gene) and Pres1, Pres2 envelop genes. Preferred mutations in this regard include one or more of sE164D, sS193L, or sI195M. The above methods are useful for detecting an agent which exhibits inhibitory activity to an HBV which exhibits resistance to one or more of TDF, LMV, a nucleoside analog other than TDF or LMV or an immunological reagent.

Accordingly, another aspect of the present invention contemplates a method for determining whether an HBV strain exhibits reduced sensitivity to a nucleoside or nucleotide analogs, or other HBV DNA polymerase antagonists and/or an immunological reagent, said method comprising isolating DNA or corresponding mRNA from said HBV and screening for a mutation in the nucleotide sequence encoding the envelope genes wherein the presence of the following mutations in the HBsAg: sE164D, sS193L, or sI195M or combinations thereof or an equivalent one or more other mutation is indicative of a variant wherein said variant exhibits a decreased sensitivity to TDF and/or LMV and optionally other nucleoside or nucleotide analogs, or other HBV DNA polymerase antagonists and/or an immunological reagent.

The present invention is predicated in part on the identification and isolation of variants of HBV that have a plurality of mutations and exhibit two or more characteristics selected from decreased or reduced sensitivity to one or more nucleoside or nucleotide analogs or other antagonists of HBV DNA polymerase activity, a reduced level and/or functional activity of Hepatitis Be antigen, or a reduced, abrogated or otherwise impaired immunological interactivity, relative to wild-type HBV. Thus, the identification of HBV variants with these mutational patterns is important inter alia for the development of assays to detect HBV variants and assays to screen for agents which are useful in treating and/or preventing infections by those variants and/or other HBV isolates and for the development of alternative therapeutic regimes for managing HBV infections.

Accordingly, one aspect of the present invention is directed to an isolated HBV variant comprising a plurality of nucleotide mutations that correlate with at least two characteristics selected from (a) resistance to one or more nucleoside or nucleotide analogs or other antagonists of HBV DNA polymerase activity, (b) a reduced level and/or functional activity of Hepatitis Be antigen, or (c) a reduced, abrogated or otherwise impaired immunological interactivity.

Another aspect of the present invention contemplates an isolated HBV variant comprising a plurality of nucleotide mutations that correlate with (a) resistance to one or more nucleoside or nucleotide analogs or other antagonists of HBV DNA polymerase activity, (b) a reduced level and/or functional activity of Hepatitis Be antigen, and (c) a reduced, abrogated or otherwise impaired immunological interactivity.

Yet another aspect of the present invention provides an isolated HBV variant comprising a plurality of nucleotide mutations selected from two or more of (a) a nucleotide mutation in a gene encoding a DNA polymerase resulting in at least one amino acid addition, substitution and/or deletion to said DNA polymerase wherein said variant exhibits decreased sensitivity to TDF and/or LMV and optionally other nucleoside or nucleotide analogs or other antagonists of HBV DNA polymerase activity, (b) a nucleotide mutation in a gene encoding a Hepatitis Be antigen or in a transcriptional control element of said gene wherein said mutation results in a reduced level and/or functional activity of said Hepatitis Be antigen, or (c) a nucleotide mutation in a gene encoding a hepatitis B polypeptide resulting in at least one amino acid addition, substitution and/or deletion to said polypeptide which reduces, abrogates or otherwise impairs its immunological interactivity.

The detection of amino acid variants of DNA polymerase is conveniently accomplished by comparison to reference sequences. The polymorphisms shown represent the variations shown in various databases for active pathogenic HBV strains. Where an HBV variant comprises an amino acid different to what is represented, then such an isolate is considered a putative HBV variant having an altered DNA polymerase activity.

The present invention further contemplates agents which inhibit TDF and/or LMV resistant HBV variants. Such agents will be particularly useful if long-term treatment by TDF and/or LMV and/or optionally other nucleoside or nucleotide analogs, or other HBV DNA polymerase antagonists and/or an immunological reagent is contemplated by the clinician. The agents may be DNA or RNA or proteinaceous or non-proteinaceous chemical molecules. Natural product screening such as from plants, coral and microorganisms is also contemplated as a useful potential source of masking agents. The agents may be in isolated form or in the form of a pharmaceutical composition and may be administered sequentially or simultaneously with the nucleoside or nucleotide analogs, or other HBV DNA polymerase antagonists and/or an immunological reagent.

Accordingly, another aspect of the present invention contemplates a method for detecting an agent which exhibits inhibitory activity to an HBV, exhibiting resistance or decreased sensitivity to TDF and/or LMV, or nucleoside analog other than TDF or LMV or an immunological reagent said method comprising:

generating a genetic construct comprising a replication competent-effective amount of the genome from said HBV contained in a plasmid vector and then transfecting said cells with said construct;

contacting said cells, before, during and/or after transfection, with the agent to be tested;

culturing said cells for a time and under conditions sufficient for the HBV to replicate, express genetic sequences and/or assemble and/or release virus or virus-like particles if resistant to said agent; and subjecting the cells, cell lysates or culture supernatant fluid to viral- or viral-component-detection means to determine whether or not the virus has replicated, expressed genetic material and/or assembled and/or been released in the presence of said agent.

Still another aspect of the present invention provides a method for detecting an agent which exhibits inhibitory activity to an HBV, exhibiting resistance or decreased sensitivity to TDF and/or LMV, or nucleoside analog other than TDF or LMV or an immunological reagent said method comprising:

generating a genetic construct comprising a replication competent-effective amount of the genome from said HBV contained in or fused to an amount of a baculovirus genome effective to infect cells and then infecting said cells with said construct;

contacting said cells, before, during and/or after infection, with the agent to be tested;

culturing said cells for a time and under conditions sufficient for the HBV to replicate, express genetic sequences and/or assemble and/or release virus or virus-like particles if resistant to said agent; and subjecting the cells, cell lysates or culture supernatant fluid to viral- or viral-component-detection means to determine whether or not the virus has replicated, expressed genetic material and/or assembled and/or been released in the presence of said agent.

Still another aspect of the present invention provides a method for detecting an agent which exhibits inhibitory activity to an HBV, exhibiting resistance or decreased sensitivity to TDF and/or LMV, or nucleoside analog other than TDF or LMV or an immunological reagent said method comprising:

generating a genetic construct comprising a replication competent-effective amount of the genome from said HBV contained in or fused to an amount of a baculovirus genome effective to infect cells and then infecting said cells with said construct;

contacting said cells, before, during and/or after infection, with the agent to be tested;

culturing said cells for a time and under conditions sufficient for the HBV to replicate, express genetic sequences and/or assemble and/or release virus or virus-like particles if resistant to said agent; and subjecting the cells, cell lysates or culture supernatant fluid to viral- or viral-component-detection means to determine whether or not the virus has replicated, expressed genetic material and/or assembled and/or been released in the presence of said agent.

Preferably, the HBV genome is stably integrated into the cells' genome.

Whilst the baculovirus vector is a particularly useful in the practice of the present invention, the subject invention extends to a range of other vectors such as but not limited to adenoviral vectors.

The present invention further extends to cell lines carrying genetic constructs comprising all or a portion of an HBV genome or a gene or part of a gene therefrom.

The present invention also provides for the use of the subject HBV variants to screen for anti-viral agents. These anti-viral agents inhibit the virus. The term "inhibit" includes antagonizing or otherwise preventing infection, replication, assembly and/or release or any intermediate step. Preferred anti-viral agents include nucleoside analogs, however, the present invention extends to non-nucleoside/non-nucleotide analog molecules.

In addition, rational drug design is also contemplated to identify or generate chemical molecules which either mimic a nucleoside or nucleotide analog or other DNA polymerase antagonist or which interact with a particular nucleotide sequence or a particular nucleotide. Combinatorial chemistry and two hybrid screening are some of a number of techniques which can be employed to identify potential therapeutic or diagnostic agents.

In one example, the crystal structure of polymerase is used to rationally design small chemical molecules likely to interact with key regions of the molecule required for function and/or antigenicity. Such agents may be useful as inhibitors of polymerase activity.

Several models of the HBV polymerase have been prepared due to the similarity with reverse transcriptase from HIV (Das et al., *J. Virol.* 75(10): 4771-4779, 2001; Bartholomeusz et al., *Antivir Ther.* 9:149-60, 2004; Allen et al., *Hepatology* 27(6): 1670-1677, 1998). The models of the HBV polymerase can be used for the rational drug design of new agents effective against HBV encoding the resistant mutations as well as wild type virus. The rational drug that is designed may be based on a modification of an existing antiviral agent such as the agent used in the selection of the HBV encoding the mutations associated with resistance. Viruses or clones expressing HBV genomic material encoding the mutations may also be used to screen for new antiviral agents.

The above methods are particularly useful in identifying an inhibitor of a TDF— and/or LMV-resistant HBV. The present invention extends, therefore, to compositions of the inhibitors. The inhibitors may also be in the form of antibodies or genetic molecules such as ribozymes, antisense molecules and/or sense molecules for co-suppression or the induction of RNAi.

The term "composition" includes a "pharmaceutical composition".

The inhibitor is referred to below as an "active ingredient" or "active compound" and may be selected from the list of inhibitors given above.

The composition may include an antigenic component of the HBV, a defective HBV variant or an agent identified through natural product screening or rational drug design (including combinatorial chemistry).

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

The pharmaceutical composition may also comprise genetic molecules such as a vector capable of transfecting target cells where the vector carries a nucleic acid molecule capable of encoding an aspartyl protease inhibitor. The vector may, for example, be a viral vector.

Pharmaceutical forms suitable for injectable use include sterile aqueous solutions (where water soluble) and sterile powders for the extemporaneous preparation of sterile injectable solutions. It must be stable under the conditions of manufacture and storage and must be preserved against the contaminating action of microorganisms such as bacteria and fungi. The carrier can be a solvent or dilution medium comprising, for example, water, ethanol, polyol (for example, glycerol, propylene glycol and liquid polyethylene glycol, and the like), suitable mixtures thereof and vegetable oils. The proper fluidity can be maintained, for example, by the use of superfactants. The preventions of the action of microorganisms can be brought about by various anti-bacterial and anti-fungal agents, for example, parabens, chlorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with the active ingredient and optionally other active ingredients as required, followed by filtered sterilization or other appropriate means of sterilization. In the case of sterile powders for the preparation of sterile injectable solutions, suitable methods of preparation include vacuum drying and the freeze-drying technique which yield a powder of active ingredient plus any additionally desired ingredient.

When the active ingredient is suitably protected, it may be orally administered, for example, with an inert diluent or with an assimilable edible carrier, or it may be enclosed in hard or soft shell gelatin capsule, or it may be compressed into tablets. For oral therapeutic administration, the active ingredient may be incorporated with excipients and used in the form of ingestible tablets, buccal tablets, troches, capsules, elixirs, suspensions, syrups, wafers and the like. Such compositions and preparations should contain at least 1% by weight of active compound. The percentage of the compositions and preparations may, of course, b varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 µg and 300 mg of active compound (TDF is administered at 300 mg single dose). Alternative dosage amounts include from about 1 µg to about 1000 mg and from about 10 µg to about 500 mg. These dosages may be per individual or per kg body weight. Administration may be per hour, day, week, month or year.

The tablets, troches, pills, capsules and the like may also contain the components as listed hereafter. A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and a flavoring. Of course, any material used in preparing any dosage unit form should be pharmaceutically pure and substantially non-toxic in the amounts employed. In addition, the active compound(s) may be incorporated into sustained-release preparations and formulations.

As stated above, the present invention further extends to an isolated HBsAg from the HBV variants herein described. More particularly, the present invention provides an HBsAg or a recombinant form thereof or derivative or chemical equivalent thereof. The isolated surface component and, more particularly, isolated surface antigen or its recombinant, derivative or chemical equivalents are useful in the development of biological compositions such as vaccine formulations.

Yet another aspect of the present invention provides a composition comprising a variant HBV resistant to TDF and/or LMV and optionally other nucleoside analogs or an HBV surface antigen from said variant HBV or a recombinant or derivative form thereof or its chemical equivalent and one or more pharmaceutically acceptable carriers and/or diluents.

As indicated above, antibodies may be generated to the mutant HBV agents and used for passive or direct vaccination against infection by these viruses. The antibodies may be generated in humans or non-human animals. In the case of the latter, the non-human antibodies may need to be deimmunized or more specifically humanized prior to use. Deimmunized may include, for example, grafting complimentary determining regions (CDRs) from the variable region of a murine or non-human animal anti-HBV antibody onto a human consensus fragment antibody binding (Fab) polypeptide. Alternatively, amino acids defining epitopes in the variable region of the antibody may be mutated so that the epitopes are no longer recognized by the human MHC II complex.

Insofar as ribozyme, antisense or co-suppression (RNAi) repression is concerned, this is conveniently aimed at post-transcription gene silencing. DNA or RNA may be administered or a complex comprising RNAi or a chemical analog thereof specific for HBV mRNA may be employed.

All such molecules may be incorporated into pharmaceutical compositions.

Generally, if an HBV is used, it is first attenuated. The biological composition according to this aspect of the present invention generally further comprises one or more pharmaceutically acceptable carriers and/or diluents.

The present invention extends to vaccines. For example, the vaccine may comprise (1) an HBV variant as described herein alone; (2) the viral variant in combination with an anti-HBV agent; and/or (3) an agent capable of inhibiting the subject HBV variants.

The present invention is further directed to the use of defective HBV variants in the manufacture of therapeutic vaccines to vaccinate individuals against infection by HBV strains having a particular nucleotide sequence or encoding a particular polymerase.

The subject invention extends to kits for assays for variant HBV resistant to TDF and/or LMV. Such kits may, for example, contain the reagents from PCR or other nucleic acid hybridization technology or reagents for immunologically based detection techniques. A particularly useful assay includes the reagents and components required for immobilized oligonucleotide- or oligopeptide-mediated detection systems.

Still another aspect of the present invention contemplates a method for determining the potential for an HBV to exhibit reduced sensitivity to TDF and/or LMV or optionally other nucleoside analogs, said method comprising isolating DNA or corresponding mRNA from said HBV and screening for a mutation in the nucleotide sequence encoding HBV DNA polymerase resulting in at least one amino acid substitution, deletion and/or addition in any one or more of domains F and A through E or a region proximal thereto of said DNA polymerase and associated with resistance or decreased sensitivity to TDF and/or LMV wherein the presence of such a mutation is an indication of the likelihood of resistance to said TDF and/or LMV.

An assessment of a potential viral variant is important for selection of an appropriate therapeutic protocol. Such an assessment is suitably facilitated with the assistance of a computer programmed with software, which inter alia adds index values ($I_V$s) for at least two features associated with the viral variants to provide a potency value ($P_A$) corresponding to the resistance or sensitivity of a viral variant to a particular chemical compound or immunological agent. The $I_V$s can be selected from (a) the ability to exhibit resistance for reduced sensitivity to a particular compound or immunological agent; (b) an altered DNA polymerase from wild-type HBV; (c) an altered surface antigen from wild-type HBV; or (d) morbidity or recovery potential of a patient. Thus, in accordance with the present invention, $I_V$s for such features are stored in a machine-readable storage medium, which is capable of processing the data to provide a $P_A$ for a particular viral variant or a biological specimen comprising same.

Thus, in another aspect, the invention contemplates a computer program product for assessing the likely usefulness of a viral variant or biological sample comprising same for determining an appropriate therapeutic protocol in a subject, said product comprising:
(1) code that receives as input $I_V$s for at least two features associated with said viral agents or biological sample comprising same, wherein said features are selected from:
 (a) the ability to exhibit resistance for reduced sensitivity to a particular compound or immunological agent;
 (b) an altered DNA polymerase from wild-type HBV;
 (c) an altered surface antigen from wild-type HBV; or
 (d) morbidity or recovery potential of a patient;
 (e) altered replication capacity (increased or decreased);
(2) code that adds said IVs to provide a sum corresponding to a $P_V$ for said viral variants or biological samples; and
(3) a computer readable medium that stores the codes.

In a related aspect, the invention extends to a computer for assessing the likely usefulness of a viral variant or biological sample comprising same in a subject, wherein said computer comprises:
(1) a machine-readable data storage medium comprising a data storage material encoded with machine-readable data, wherein said machine-readable data comprise $I_V$s for at least two features associated with said viral variant or biological sample; wherein said features are selected from:—

(a) the ability to exhibit resistance for reduced sensitivity to a particular compound or immunological agent;
(b) an altered DNA polymerase from wild-type HBV;
(c) an altered surface antigen from wild-type HBV; or
(d) morbidity or recovery potential of a patient;
(e) altered replication capacity (increased or decreased);
(2) a working memory for storing instructions for processing said machine-readable data;
(3) a central-processing unit coupled to said working memory and to said machine-readable data storage medium, for processing said machine readable data to provide a sum of said $I_i$s corresponding to a $P_V$ for said compound(s); and
(4) an output hardware coupled to said central processing unit, for receiving said $P_V$.

Figure 2:
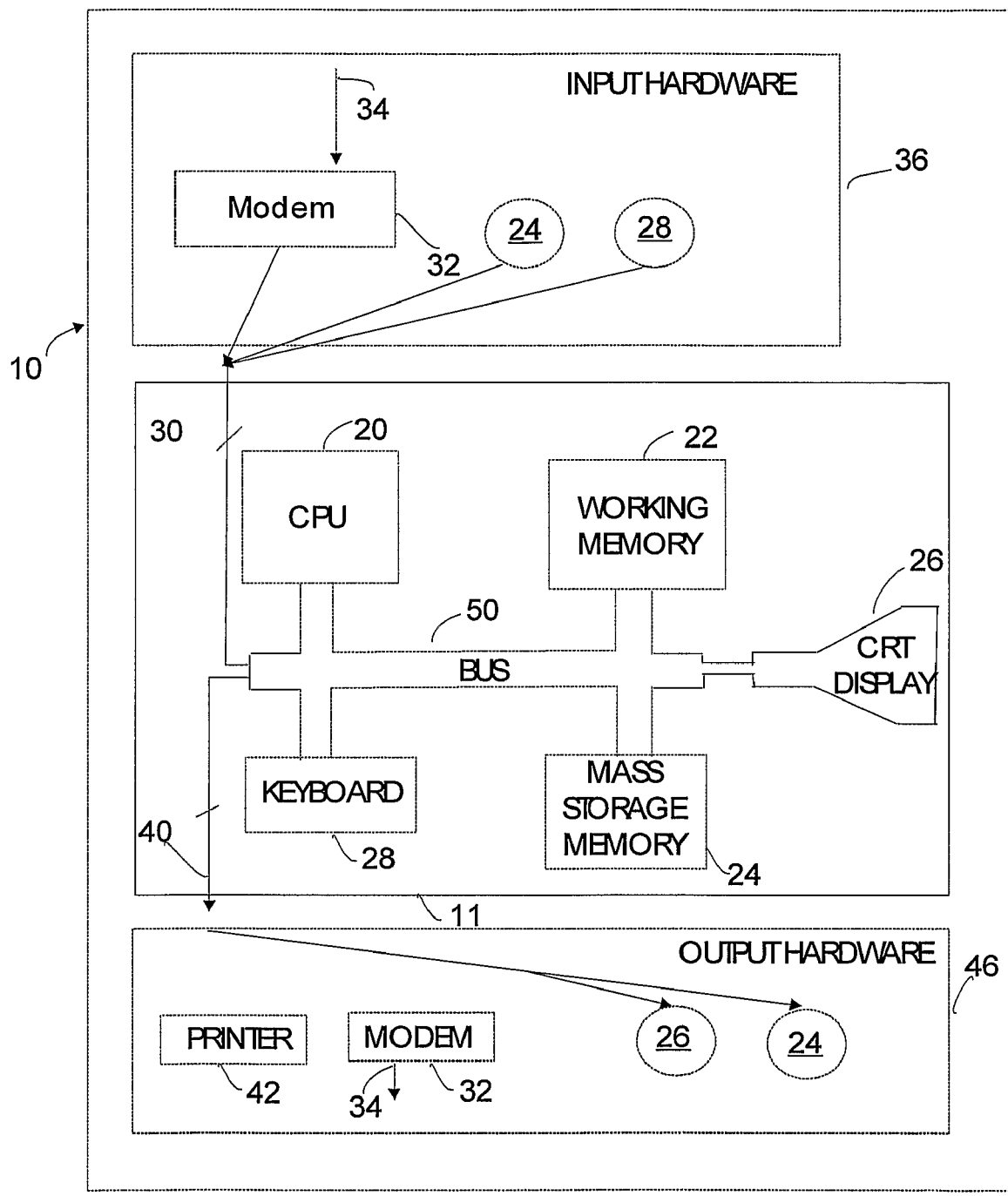
FIG. 2 is a diagrammatic representation of a computer system for determining the potency value ($P_A$) of a variant HBV.

Any general or special purpose computer system is contemplated by the present invention and includes a processor in electrical communication with both a memory and at least one input/output device, such as a terminal. Such a system may include, but is not limited to, personal computers, work stations or mainframes. The processor may be a general purpose processor or microprocessor or a specialised processor executing programs located in RAM memory. The programs may be placed in RAM from a storage device, such as a disk or pre-programmed ROM memory. The RAM memory in one embodiment is used both for data storage and program execution. The computer system also embraces systems where the processor and memory reside in different physical entities but which are in electrical communication by means of a network. For example, a computer system having the overall characteristics set forth in FIG. 2 may be useful in the practice of the instant invention. More specifically, FIG. 2 is a schematic representation of a typical computer work station having in electrical communication (100) with one another via, for example, an internal bus or external network, a processor (101), a RAM (102), a ROM (103), a terminal (104), and optionally an external storage device, for example, a diskette, CD ROM, or magnetic tape (105).

The present invention further provides a kit.

In one embodiment, the present invention provides a kit for an assay for variant HBV resistant to TDF, LMV, a nucleoside analog other than TDF or LMV or an immunological reagent said kit comprising the reagents from PCR or other nucleic acid hybridization technology or reagents for immunologically based detection techniques.

The present invention is further described by the following non-limiting Examples.

Example 1

Overlapping Genome of HBV

The overlapping genome of HBV is represented in FIG. 1. The gene encoding DNA polymerase (P), overlaps the viral envelope genes, Pre-S1 and Pre-S2, and partially overlaps the X and core (C) genes. The HBV envelope comprises small, middle and large HBV surface antigens. The large protein component is referred to as the HBV surface antigen (HBsAg) and is enclosed by the S gene sequence. The Pre-S1 and Pre-S2 gene sequences encode the other envelope components.

Example 2

Patient and Treatment

A total of 20 (47%) individuals were infected with WT HBV RT despite prolonged exposure to LMV and TDF, whilst of the remaining 23 (53%), two selected de novo mutations known to be associated with LMV resistance, 19 showed the same LMV-associated mutations already present at baseline, and 2 patients reverted to WT. Overall, 6 distinct LMV mutational patterns were observed (see Table 3) rtL180M+rtM204V, rtL180M+rtM204V+rtV207M/I, rtV173L+rtL180M+rtM204V, rtL180M+rtM204I, rtM204I and rtV191I.

Two patients selected viruses with novel mutations (see Table 3), both were HBeAg positive and genotype A.

TABLE 3

Mutational patterns of the HBV pol in 23 HBV/HIV-coinfected individuals exposed to tenofovir for longer than 6 months.

| Pattern | No. of patients | Mutational pattern |
|---|---|---|
| A | 10 | rtL180M + rtM204V |
| B | 4 | rtL180M + rtM204V + V207M/I |
| C | 4 | rtV173L + rtL180M + rtM204V |
| D | 1 | rtL180M + rtM204I |
| E | 1 | rM204I |
| F | 1 | rtV191I |
| G | 1 | *rtA194T* + rtL180M + rtM204V |
| H | 1 | *rtA194T* + rtV173L + rtL180M + rtM204V |

Patterns A-F correspond to lamivudine resistance while patterns G-H correspond to novel mutational patterns. Italic represents the novel amino acid change.

Patient A:

31 year old male, HIV+, HBsAg+, was treatment at Hospital Carlos III, Madrid, with DDI, TDF+LPV/r. After 36 weeks therapy changed to AZT, 3TC, TDP+LPV/r. After commencing treatment, plasma HIV RNA remained below detectable levels (<50 cop/mL) and absolute CD4 counts steadily increased from 224 to 594 cel/uL (% from 7% to 22%). The patient is infected with HBV genotype A, positive for HBeAg, antiHBc, and negative for antiHBs, antiHBc IgM. Plasma HBV DNA and ALT were measured every 3-4 months. HBV DNA was measured using Roche COBAS Monitor (see Table 4).

TABLE 4

The HIV and HBV DNA viral load and Liver function test (alanine transaminase; ALT) for Patient A

| week | HIV (cop/mL) | HBV (cop/mL) | ALT (IU/mL) |
|---|---|---|---|
| 79 | <200 | <50 | 56 |
| 62 | 300 | <50 | 41 |
| 48 | 1000 | <50 | 212 |
| 36 | 700 | <50 | 29 |
| 16 | 13000 | <50 | 46 |
| 0 | | <50 | 41 |
| −8 | | 34966 | 61 |

Figure 17:
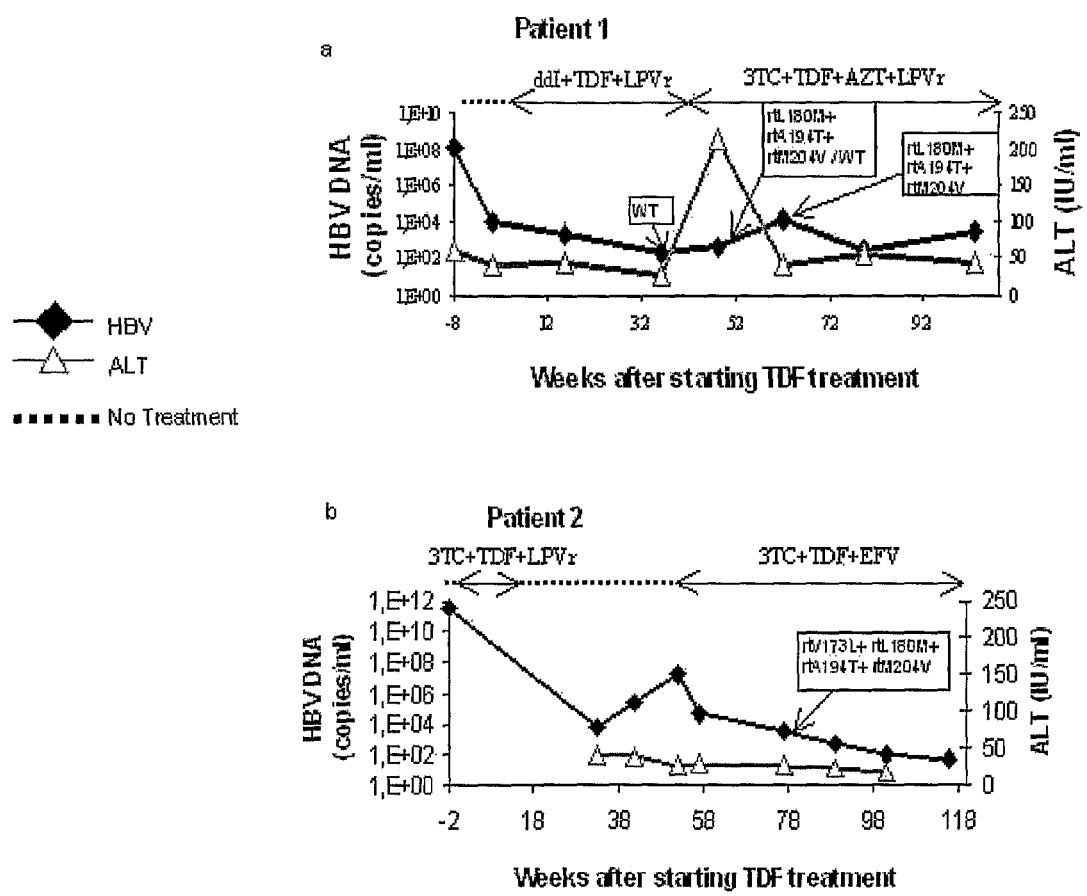
FIG. 17 is a graphical representation showing HBV DNA version TDF treatment in (a) Patient A and (b) Patient B.

Patient B:

44 year old male, HIV+, HBsAg+, HAV+, started treatment in 1995 with AZT and DDC (see Table 4 for AntiRetroviral therapy history). Patient B presented with mutations in the HBV RT of rtV173L, rtA194T, rtL180M and rtM204V, 77 weeks after the start of TDF therapy. He had initiated his treatment with zidovudine and zalcitabine in 1995. Treatment with TDF along with LMV and lopinavir boosted with ritonavir was prescribed in 2002. After 8 weeks, the patient voluntarily stopped therapy for 37 weeks. Antiretroviral treatment was resumed with TDF, LMV and efavirenz. Plasma HBV-DNA decreased from 7.2 log copies/ml to 1.7 log copies/ml in 64 weeks after restart of ART. During this period, ALT levels remained constantly normal and CD4+ counts ranged from 315 to 553 cells/µl, always with undetectable plasma HIV-RNA levels during treatment (FIG. 17b).

TABLE 5

Antiviral History for Patient B

| HAART | Week |
|---|---|
| AZT/ddC | −338 |
| ddI/3TC | −308 |
| ddI/3TC/IDV | −286 |
| D4T/ddI/NVP | −142 |
| D4T/3TC/ABC | −111 |
| D4T/ABC/APVr | −100 |
| D4T/APVr | −96 |
| D4T/3TC/LPVr | −49 |
| ddI/3TC/LPVr | −45 |
| 3TC/LPVr | −1 |
| TDF/3TC/LPVr | 0 |
| No treatment | 33 |
| TDF/3TC/EFV | 46 |

After treatment with TDF, HIV RNA, HBV DNA and ALT were measured and levels are listed in Table 6. Absolute CD4 counts ranged from 324 to 602 cel/uL (mean 457 cel/uL) (mean CD4%; 13%). The patient was infected with HBV genotype A, and was HBeAg+.

TABLE 6

HIV RNA, HBV DNA and ALT Levels

| week | HIV (cop/mL) | HBV (cop/mL) | ALT (IU/mL) |
|---|---|---|---|
| 116 | 50 | 48 | N.D. |
| 101 | 50 | 84 | 18 |
| 89 | 50 | 479 | 23 |
| 77 | 50 | 3840 | 26 |
| 57 | 50 | 39700 | 30 |
| 52 | 50 | 18600000 | 26 |
| 42 | 5120 | 200000 | 37 |
| 33 | 2430 | 7440 | 40 |
| −2 | 50 | 3.49E+11 | |

Example 3

Detection of Viral Markers

Hepatitis B surface antigen (HBsAg), hepatitis Be antigen (HBeAg), anti-HBe and hepatitis B core antigen (HBcAg) specific IgG and IgM were measured using commercially available immunoassays. Hepatitis B viral DNA levels were measured using Roche COBAS Monitor assay according to the manufacturer's directions.

Example 4

Sequencing of HBV DNA

HBV DNA was extracted and sequenced using standard published methods. The following primers were used for amplification and sequencing:

```
                                            (SEQ ID NO: 1)
(5'-3') Primer 1 forward: TCTTGTTGACAAGAATCCTCAC, (SEQ ID NO: 2)
(5'-3') Primer 2 forward: AGACTCGTGGTGGACTTCTCT (SEQ ID NO: 3)
(5'-3') Primer 3 reverse: CCCAAAAGACCCACAATTC,
and (SEQ ID NO: 4)
(5'-3') Primer 4 reverse: TGACATACTTTCCAATCAAT.
```

Both 1st and 2nd round PCR conditions were as follows: 2 min 95 C, (30 sec 95 C, 30 sec 50 C, 90 sec 72 C)×30 cycles, 72 C for 4 mins.

Example 5

Analysis of HBV DNA

Patient A:

At week 48 the patient had no mutations associated to resistance nor any novel amino-acid changes. However, at week 62 the patient selected mutations rtL180M and rtM204V as well as a novel mutation rtA194T. See Table 7.

Patient B:

No sera for sequence analysis was available before the treatment with TDF commenced, but at week 77 the patient presented mutations rtV173L, rtL180M and rtM204V together with novel mutation rtA194T. The HBsAg mutations included sE164D, sS193L and sI195M. See Table 8.

TABLE 7

Summary of HBV mutations in patient A treated with TDF and LMV

| Sample name | Genotype | Polymerase* | Surface |
|---|---|---|---|
| 0 | A | rtS54T | — |
| 48 | A | rtS54T | — |
| 62 | A | rtL180M<br>rtA194T<br>rtM204V | sI195M |

Nomenclature according to Stuyver et al., 2001, supra

TABLE 8

Summary of HBV mutations in patient B treated with TDF and LMV

| Sample name | Genotype | Polymerase* | Surface |
|---|---|---|---|
| 77 | A | rtV173L<br>rtL180M<br>rtA194T<br>rtM204V | sE164D<br>sS193L<br>sI195M |

Example 6

Modelling of the HBV Polymerase with rtA194T

The HBV polymerase has not been crystallized and a homology model based on similarity with HIV has been developed (Bartholomeusz et al, 2004 supra). Using this model mutations were located at rtA194T.

Figure 15:
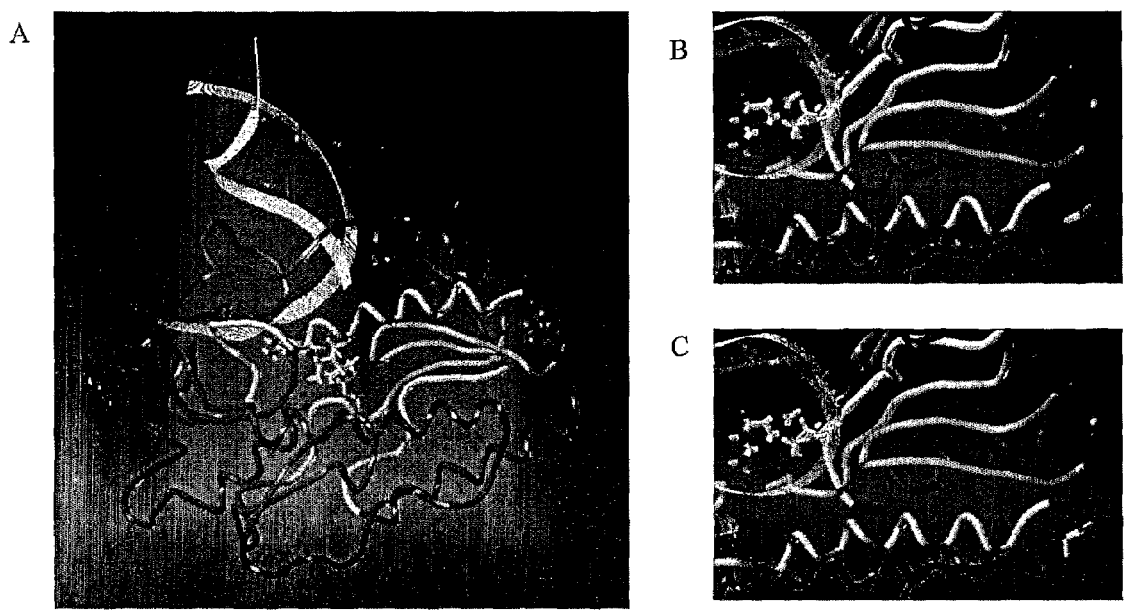
FIG. 15 is a diagrammatic representation of the HBV polymerase. Residue aa194 from the wild type is highlighted in FIG. 15b. Residue aa194T is highlighted in FIG. 15c.

The HBV reverse transcriptase mutation rtA194T is located away from the active site towards the end of the alpha helix in a potential hinge region which contains the B domain (FIG. 15).

Two potential mechanisms by which the mutation at rtA194T may influence resistance to TDF and/or LMV.

1. The mutation at rtA194T in the hinge region may still have the ability to affect the position alpha helix that encodes the B domain. This is where codon rt180 is located, and this region has the potential to interact with the DNA template. Changes to this region may alter the position of the DNA template strand relative to the dNTP binding site.
2. The reverse transcriptase (rt) region is only part of the polymerase protein. The entire HBV polymerase is a large protein (90 kd). The mutation is on the external surface of the rt region. There is no structural homologues for the terminal protein and spacer region components of the HBV polymerase protein that also includes an RNase H component. Therefore, the mutation has the potential to interact with the rest of components the polymerase protein. This has been demonstrated in HIV in which mutations which affect the RNAse H component have been known to also alter antiviral sensitivity.

Example 7

TDF

Figure 16:
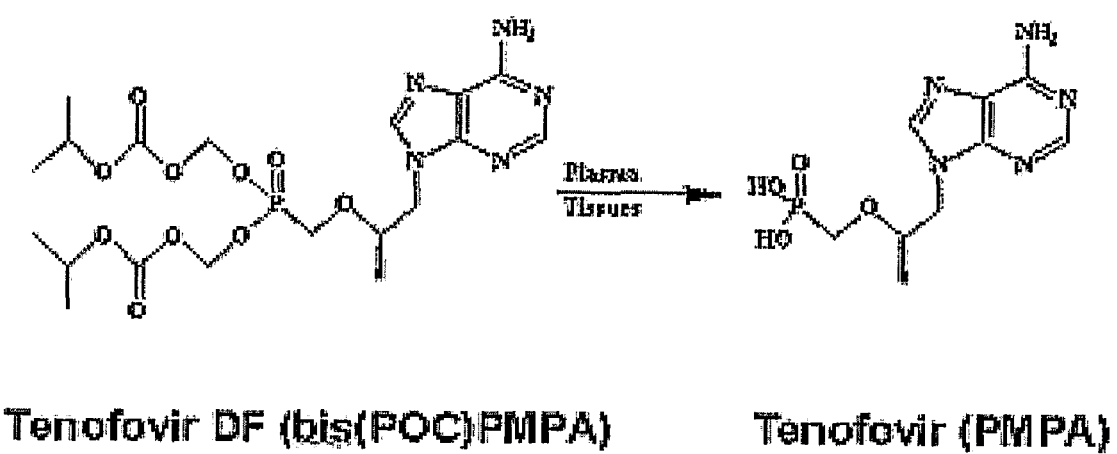
FIG. 16 is a diagrammatic representation of the chemical structure of TDF.

TDF is a potent inhibitor of HBV replication. TDF has activity against hepadnaviruses and HIV. The structure of TDF is shown in FIG. 16 and its synthesis is described in a review by Grim S A, Romanelli F, *Ann Pharmacother* 37(6): 849-59, 2003. Preclinical studies indicate that TDF is a highly potent inhibitor of HBV in enzyme- and cell-based assays.

Example 8

Replication Competent HBV Plasmids

An extended (1.28×) HBV genome was cloned (HBV genotype A, subtype adw2) into a pBluescript KS (+) plasmid (Stratagene, La Jolla, Calif., USA), as described by Tacke et al, *J Virol* 78:8524-8535, 2004.

Example 9

Site-Directed Mutagenesis

Three mutated HBV plasmids were constructed using a Quikchange (Registered) II site-directed mutagenesis kit (Stratagene, La Jolla, Calif., USA). Plasmids contained either mutations rtL180M and rtM204V (LM), rtL180M, rtM204V and rtA194T (LMAT), or rtA194T (AT). To create LAM-specific mutations rtL180M and rtM204V, primers rtM204VF (CTT TCA GCT ATG TGG ATG ATG TGG TAT TGG (SEQ ID NO:17)) and rtM204VR (CCA ATA CCA CAT CAT CCA CAT AGC TGA AAG (SEQ ID NO:18)), and rtL180MF (TCC GTT TCT CAT GGC TCA GTT TAC TAG TG (SEQ ID NO:19)) and rtL180MR (CAC TAG TAA ACT GAG CCA TGA GAA ACG GA (SEQ ID NO:20)), respectively, were designed. Mutations were created according to Bock et al, *Gastroenterology* 122:264-273, 2002.

Mutation rtA194T was engineered using mutagenic primers A194TR (AGT GGT TCG TAG GAC TTT CCC CCA CTG TTT GG (SEQ ID NO:21)) and A194TF (AGC CAA ACA GTG GGG GAA AGT CCT ACG AAC CAC (SEQ ID NO:22)). All plasmids were ultimately sequenced to verify that only the intended mutations had been introduced.

Example 10

Cell Culture and Viral Transfection

HepG2 cells were grown in Eagles minimum essential medium (LGC Promochem, Middlesex, UK), supplemented with 10% v/v fetal bovine serum at 37° C. and 5% v/v $CO_2$. For cDNA transfections, $3 \times 10^5$ cells were seeded to semi-confluence onto each well of a 6-well plate and allowed to adhere overnight. The following day, 950 ng of HBV cDNA plasmid was co-transfected with 50 ng of pCMV β-Galactosidase vector (Promega, Mannheim, Germany) into each well, using the Fugene6 transfection agent and following the manufacturer's instructions (Roche, Indianapolis, USA). Five hours after transfection, cells were washed with PBS and the culture medium was replaced with media containing TDF at concentrations from 0 to 100 μM. Seventy-two hours after transfection, the cells were washed and the media changed again with the appropriate drug concentrations Media and cell lysates were harvested for analysis 5 days after transfection. Transfection efficiency was controlled by measuring β-galactosidase activity from cell lysates according to manufacturer's instructions (Promega).

Example 11

Quantification of Extracellular HBV-DNA

HBV viral particles from the cell culture supernatant were precipitated using 26% polyethylene glycol (PEG 8000, Sigma, St. Louis, Mo., USA), followed by DNase 1 digestion (Takara, Shiga, Japan). DNA was extracted using a QiaAMP viral DNA extraction kit (Qiagen). A quantitative real-time PCR was used to quantify HBV-DNA. Briefly, a 189-bp fragment of the X region was amplified in a LightCycler system (Roche), using the QuantiTect Probe PCR kit (Qiagen) and the following probes and primers: 3FL-XHybprobe (5'-ACG GGG CGC ACC TCT CTT TAC GCG G fluorescein-3' (SEQ ID NO:23)), 5LC-Xhybprobe (5'LCRed 640 nm-CTC CCC GTC TGT GCC TTC TCA TCT GC PH-3' (SEQ ID NO:24)), X sense (5'-GAC GTC CTT TGT YTA CGT CCC GTC-3' (SEQ ID NO:25)), and X antisense (5'-TGC AGA GGT GAA GCG AAG TGC ACA-3' (SEQ ID NO:26)). The LightCycler program consisted of an initial activation step (95° C., 15 min, slope 20° C./sec), 40 cycles of amplification with touch down (95° C. 10 sec, 62-55° C. 15 sec, 72° C. 13 sec, slope of 5° C./sec), melting curve (cooling from 95° C. to 50° C. for 10 sec with a slope of 20° C./sec and heating again to 95° C. for 0 sec with a slope of 0.1° C./sec), and cooling (40° C. for 30 sec with a slope of 20° C./sec). Standard dilutions of a plasmid containing the HBV X gene (X-pScript, Stratagene) were used to generate a standard curve. All measurements were carried out in triplicate.

After adjusting for transfection efficiency, $IC_{50}$ values were calculated from the HBV viral load using the following formula (Vandamme et al, *Antiviral methods and protocols:* 231, 2000):

$$\log IC_{50} = \log \text{conc. HPP} - [(HPP-50)/(HPP-LPP)] \times \log d$$

HPP, highest protective percentage; LPP, lowest protective percentage; d, dilution.

Example 12

Toxicity Determination

The toxicity of TDF was measured by transfecting HepG2 cells in 96-wells plates and continually exposing the test drugs up to 10 mM for 5 days. MTT [3-(4,5-dimethylthiazol-2-yl)-2,5-diphenyltetrazolium bromide] was added to each well at a final concentration of 500 μg/mL five hours before dissolving crystals in 200 uL of DMSO and measuring at 550 nm UV wavelengths.

Example 13

Phenotypic Analyses

Following the genetic analysis, further analyses of the novel mutations observed in the two patients described above were undertaken. As the clinical data suggested a particular relevance of the novel rtA194T mutation, especially in combination with LMV resistance, site-directed mutagenesis was performed and 3 replication-competent HBV plasmids carrying the following mutations: rtL180M+rtM204V (LM), rtL180M+rtA194T+rtM204V (LMAT), and rtA194T (AT) were constructed. The antiviral activity of TDF was examined in a transient transfection cell culture assay system along side a WT construct as described above.

Extracellular HBV-DNA was examined by real-time PCR, 5 days post-transfection and $IC_{50}$ values were calculated. The results are summarized in Table 9, which shows the resistance profile for the mutant HBV.

TABLE 9

$IC_{50}$ values for tenofovir obtained from transient transfection cell culture assays using WT and mutant HBV-DNA constructs transfected into HepG2 cells. Effect of clinical mutations on HBV susceptibility to tenofovir in vitro.

| | Extracellular DNA | |
|---|---|---|
| | $IC_{50}$ (μmol/L) | Fold $IC_{50}$ |
| WT | 12.4 | 1 |
| A194T (AT) | 95 | 7.6[a] |
| L180M + M204V (LM) | 71 | 5.7[a] |
| L180M, A194T, M204V (LMAT) | >120* | >10*[b] |

*$IC_{50}$ values above the cell toxic level of tenofovir.
[a]5-10 fold increase in the $IC_{50}$ confers to partial resistance [24]
[b]>10-fold increase in the $IC_{50}$ confers to resistance [24]

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Allen et al., *Hepatology* 27(6): 1670-1677, 1998
Aye et al., *J Hepatol.* 26: 1148-53, 1997
Bartholomeusz et al., *Antivir Ther.* 9(2):149-160, 2004
Bock et al, *Gastroenterology* 122:264-273, 2002
Boyd et al., *Antiviral Chem Chemother.* 32: 358-363, 1987
Das et al., *J. Virol.* 75(10): 4771-4779, 2001
Delaney et al., *Antimicrob Agents Chemother* 45(6): 1705-1013, 2001
Dienstag et al., *New England J Med* 333: 1657-1661, 1995
Gaillard et al., *Antimicrob Agents Chemother.* 46(4): 1005-1013, 2002
Grim S A, Romanelli F, *Ann Pharmacother.;* 37(6):849-59, 2003
Kruger et al., *Hepatology* 22: 219A, 1994
Main et al., *J Viral Hepatitis* 3: 211-215, 1996
Lada O et al., *Antivir Ther.;* 9:353-63, 2004
Norder et al., *J. Gen. Virol.* 74: 341-1348, 1993
Ren and Nassal, *J. Virol.* 75(3): 1104-1116, 2001
Severini et al., *Antimicrobial Agents Chemother* 39: 1430-1435, 1995
Shaw J P et al., *Pharm Res.* 14(12):1824-9, 1997
Stuyver et al., *Hepatology* 33: 751-757, 2001
Summers and Mason, *Cell* 29: 403-415, 1982
Tacke et al, *J Virol* 78:8524-8535, 2004
Vandamme et al, *Antiviral methods and protocols:* 231, 2000
Vere Hodge, *Antiviral Chem Chemother* 4: 67-84, 1993
Ying C et al., *J Viral Hepat.* 7(2):161-5, 2000
Xiong et al., *Hepatology.* 28(6): 1669-73, 1998

What is claimed is:

1. An isolated Hepatitis B virus (HBV) variant or genome thereof comprising nucleotide mutations in a nucleic acid sequence encoding a reverse transcriptase (rt) portion of an HBV DNA polymerase, which result in amino acid substitutions in said reverse transcriptase from:
   leucine (L) to methionine (M) at amino acid 180 (rtL180M);
   alanine (A) to threonine (T) at amino acid 194 (rtA194T); and
   methionine (M) to valine (V) at amino acid 204 (rtM204V);
wherein the foregoing amino acid substitutions are numbered with reference to M of the YMDD motif in HBV DNA polymerase being amino acid number 204, and wherein said variant exhibits decreased sensitivity to tenofovir disoproxil fumarate (TDF).

2. The isolated HBV variant or genome of claim 1, wherein said variant further exhibits reduced sensitivity to lamivudine (LMV).

3. The isolated HBV variant or genome of claim 1, wherein said variant or genome further comprises a nucleotide mutation resulting in an amino acid substitution from valine (V) to leucine (L) at amino acid 173 (rtV173L) of said reverse transcriptase portion of the DNA polymerase.

4. The isolated HBV variant or genome of claim 1, wherein said nucleotide mutations also result in an amino acid substitution from serine (S) to leucine (L) at amino acid 193 (sS193L) of said Hepatitis B surface antigen (HBsAg).

5. The isolated HBV variant or genome of claim 4, wherein the variant further exhibits decreased sensitivity to an antibody to a surface component of HBV.

6. The isolated HBV variant or genome of claim 5, wherein the surface component is the hepatitis B surface antigen (HBsAg).

7. The isolated HBV variant or genome of claim 4, wherein said nucleotide mutations further result in an amino acid substitution from glutamate (E) to aspartate (D) at amino acid 164 (sE164D) of said HBsAg of said HBV variant.

8. The isolated HBV variant or genome of claim 4, wherein said nucleotide mutations further result in an amino acid substitution from isoleucine (I) to methionine (M) at amino acid 195 (sI195M) of said HBsAg of said HBV variant.

9. A method for determining the potential for an HBV to exhibit reduced sensitivity to TDF and/or LMV said method comprising isolating DNA or corresponding mRNA from said HBV and screening for mutations in a gene encoding a reverse transcriptase (rt) portion of an HBV DNA polymerase resulting in amino acid substitutions in said reverse transcriptase from:
   leucine (L) to methionine (M) at amino acid 180 (rtL180M);
   alanine (A) to threonine (T) at amino acid 194 (rtA194T); and methionine (M) to valine (V) at amino acid 204 (rt M204V);

wherein the presence of such a mutation is indicative of reduced sensitivity to TDF and/or LMV.

10. The method of claim 9, further comprising identifying a nucleotide mutation resulting in an amino acid substitution from valine (V) to leucine (L) at amino acid 173 (rtV173L) of said reverse transcriptase portion of the DNA polymerase.

11. An immunogenic composition comprising the isolated HBV variant or genome of claim 1 and one or more pharmaceutically acceptable carriers and/or diluents.

* * * * *

SEQUENCE LISTING

```
<160> NUMBER OF SEQ ID NOS: 26

<210> SEQ ID NO 1
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 1
tcttgttgac aagaatcctc ac                                              22

<210> SEQ ID NO 2
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 2
agactcgtgg tggacttctc t                                               21
```

```
<210> SEQ ID NO 3
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 3
cccaaaagac ccacaattc                                                19

<210> SEQ ID NO 4
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 4
tgacatactt tccaatcaat                                               20

<210> SEQ ID NO 5
<211> LENGTH: 754
<212> TYPE: DNA
<213> ORGANISM: Hepatitis B Virus

<400> SEQUENCE: 5 tctagggga tcacccgtgt gtcttggcca aaattcgcag tccccaacct ccaatcactc    60
accaacctcc tgtcctccaa tttgtcctgg ttatcgctgg atgtgtctgc ggcgttttat   120
catattcctc ttcatcctgc tgctatgcct catcttctta ttggttcttc tggattatca   180
aggtatgttg cccgtttgtc ctctaattcc aggatcaaca caaccagta cgggaccatg    240 caaaacctgc acgactcctg ctcaaggcaa ctctatgttt ccctcatgtt gctgtacaaa   300
acctacggat ggaaattgca cctgtattcc catcccatcg tcctgggctt cgcaaaata   360 cctatgggag tgggcctcag tccgtttctc ttggctcagt ttactagtgc catttgttca   420
gtggttcgta gggctttccc ccactgtttg gctttcagct atatggatga tgtggtattg   480
ggggccaagt ctgtacagca tcgtgagtcc ctttataccg ctgttaccaa ttttctttg    540 tctctgggta tacatttaaa ccctaacaaa acaaaaagat ggggttattc cctaaacttc   600
atgggttaca taattggaag ttggggaaca ttgccacagg atcatattgt acaaaagatc   660
aagcactgtt ttagaaaact tcctgttaac aggcctattg attggaaagt atgtcaaaga   720
attgtgggtc ttttgggctt tgctgctcca ttta                              754

<210> SEQ ID NO 6
<211> LENGTH: 251
<212> TYPE: PRT
<213> ORGANISM: Hepatitis B Virus

<400> SEQUENCE: 6

Ser Arg Gly Ile Thr Arg Val Ser Trp Pro Lys Phe Ala Val Pro Asn
1               5                   10                  15

Leu Gln Ser Leu Thr Asn Leu Leu Ser Ser Asn Leu Ser Trp Leu Ser
            20                  25                  30

Leu Asp Val Ser Ala Ala Phe Tyr His Ile Pro Leu His Pro Ala Ala
        35                  40                  45

Met Pro His Leu Leu Ile Gly Ser Ser Gly Leu Ser Arg Tyr Val Ala
    50                  55                  60

Arg Leu Ser Ser Asn Ser Arg Ile Asn Asn Asn Gln Tyr Gly Thr Met
65                  70                  75                  80
```

Gln Asn Leu His Asp Ser Cys Ser Arg Gln Leu Tyr Val Ser Leu Met
                85                  90                  95

Leu Leu Tyr Lys Thr Tyr Gly Trp Lys Leu His Leu Tyr Ser His Pro
            100                 105                 110

Ile Val Leu Gly Phe Arg Lys Ile Pro Met Gly Val Gly Leu Ser Pro
            115                 120                 125

Phe Leu Leu Ala Gln Phe Thr Ser Ala Ile Cys Ser Val Val Arg Arg
130                 135                 140

Ala Phe Pro His Cys Leu Ala Phe Ser Tyr Met Asp Asp Val Val Leu
145                 150                 155                 160

Gly Ala Lys Ser Val Gln His Arg Glu Ser Leu Tyr Thr Ala Val Thr
                165                 170                 175

Asn Phe Leu Leu Ser Leu Gly Ile His Leu Asn Pro Asn Lys Thr Lys
            180                 185                 190

Arg Trp Gly Tyr Ser Leu Asn Phe Met Gly Tyr Ile Ile Gly Ser Trp
            195                 200                 205

Gly Thr Leu Pro Gln Asp His Ile Val Gln Lys Ile Lys His Cys Phe
210                 215                 220

Arg Lys Leu Pro Val Asn Arg Pro Ile Asp Trp Lys Val Cys Gln Arg
225                 230                 235                 240

Ile Val Gly Leu Leu Gly Phe Ala Ala Pro Phe
                245                 250

<210> SEQ ID NO 7
<211> LENGTH: 185
<212> TYPE: PRT
<213> ORGANISM: Hepatitis B Virus

<400> SEQUENCE: 7

Leu Gly Gly Ser Pro Val Cys Leu Gly Gln Asn Ser Gln Ser Pro Thr
1               5                   10                  15

Ser Asn His Ser Pro Thr Ser Cys Pro Pro Ile Cys Pro Gly Tyr Arg
                20                  25                  30

Trp Met Cys Leu Arg Arg Phe Ile Ile Phe Leu Phe Ile Leu Leu Leu
            35                  40                  45

Cys Leu Ile Phe Leu Leu Val Leu Leu Asp Tyr Gln Gly Met Leu Pro
50                  55                  60

Val Cys Pro Leu Ile Pro Gly Ser Thr Thr Thr Ser Thr Gly Pro Cys
65                  70                  75                  80

Lys Thr Cys Thr Thr Pro Ala Gln Gly Asn Ser Met Phe Pro Ser Cys
                85                  90                  95

Cys Cys Thr Lys Pro Thr Asp Gly Asn Cys Thr Cys Ile Pro Ile Pro
            100                 105                 110

Ser Ser Trp Ala Phe Ala Lys Tyr Leu Trp Glu Trp Ala Ser Val Arg
            115                 120                 125

Phe Ser Trp Leu Ser Leu Leu Val Pro Phe Val Gln Trp Phe Val Gly
130                 135                 140

Leu Ser Pro Thr Val Trp Leu Ser Ala Ile Trp Met Met Trp Tyr Trp
145                 150                 155                 160

Gly Pro Ser Leu Tyr Ser Ile Val Ser Pro Phe Ile Pro Leu Leu Pro
                165                 170                 175

Ile Phe Phe Cys Leu Trp Val Tyr Ile
            180                 185

<210> SEQ ID NO 8

```
<211> LENGTH: 746
<212> TYPE: DNA
<213> ORGANISM: Hepatitis B Virus

<400> SEQUENCE: 8 tctagggga tcacccgtgt gtcttggcca aaattcgcag tccccaacct ccaatcactc      60
accaacctcc tgtcctccaa tttgtcctgg ttatcgctgg atgtgtctgc ggcgttttat    120
catattcctc ttcatcctgc tgctatgcct catcttctta ttggttcttc tggattatca    180
aggtatgttg cccgtttgtc tctaattcc aggatcaaca caaccagta cgggaccatg     240
caaaacctgc acgactcctg ctcaaggcaa ctctatgttt ccctcatgtt gctgtacaaa   300
acctacggat ggaaattgca cctgtattcc catcccatcg tcctgggctt cgcaaaata    360
cctatgggag tgggcctcag tccgtttctc ttggctcagt ttactagtgc catttgttca   420
gtggttcgta gggcttttcc ccactgtttg ctttcagct atatggatga tgtggtattg   480
ggggccaagt ctgtacagca tcgtgagtcc ctttataccg ctgttaccaa tttttctttg   540
tctctgggta tacatttaaa ccctaacaaa acaaaaagat ggggttattc cctaaacttc   600
atgggytaca taattggaag ttggggaaca ttgccacagg atcatattgt acaaaagatc   660
aaacactgtt ttagaaaact tcctgttaac aggcctattg attggaaagt atgtcaaaga   720
attgtgggtc ttttgggctt tgctgc                                        746

<210> SEQ ID NO 9
<211> LENGTH: 248
<212> TYPE: PRT
<213> ORGANISM: Hepatitis B Virus

<400> SEQUENCE: 9

Ser Arg Gly Ile Thr Arg Val Ser Trp Pro Lys Phe Ala Val Pro Asn
1               5                   10                  15

Leu Gln Ser Leu Thr Asn Leu Leu Ser Ser Asn Leu Ser Trp Leu Ser
            20                  25                  30

Leu Asp Val Ser Ala Ala Phe Tyr His Ile Pro Leu His Pro Ala Ala
        35                  40                  45

Met Pro His Leu Leu Ile Gly Ser Ser Gly Leu Ser Arg Tyr Val Ala
    50                  55                  60

Arg Leu Ser Ser Asn Ser Arg Ile Asn Asn Gln Tyr Gly Thr Met
65                  70                  75                  80

Gln Asn Leu His Asp Ser Cys Ser Arg Gln Leu Tyr Val Ser Leu Met
            85                  90                  95

Leu Leu Tyr Lys Thr Tyr Gly Trp Lys Leu His Leu Tyr Ser His Pro
        100                 105                 110

Ile Val Leu Gly Phe Arg Lys Ile Pro Met Gly Val Gly Leu Ser Pro
    115                 120                 125

Phe Leu Leu Ala Gln Phe Thr Ser Ala Ile Cys Ser Val Val Arg Arg
130                 135                 140

Ala Phe Pro His Cys Leu Ala Phe Ser Tyr Met Asp Asp Val Val Leu
145                 150                 155                 160

Gly Ala Lys Ser Val Gln His Arg Glu Ser Leu Tyr Thr Ala Val Thr
            165                 170                 175

Asn Phe Leu Leu Ser Leu Gly Ile His Leu Asn Pro Asn Lys Thr Lys
        180                 185                 190

Arg Trp Gly Tyr Ser Leu Asn Phe Met Gly Tyr Ile Ile Gly Ser Trp
    195                 200                 205

Gly Thr Leu Pro Gln Asp His Ile Val Gln Lys Ile Lys His Cys Phe
```

```
                210                 215                 220
Arg Lys Leu Pro Val Asn Arg Pro Ile Asp Trp Lys Val Cys Gln Arg
225                 230                 235                 240

Ile Val Gly Leu Leu Gly Phe Ala
                245

<210> SEQ ID NO 10
<211> LENGTH: 185
<212> TYPE: PRT
<213> ORGANISM: Hepatitis B Virus

<400> SEQUENCE: 10

Leu Gly Gly Ser Pro Val Cys Leu Gly Gln Asn Ser Gln Ser Pro Thr
1               5                   10                  15

Ser Asn His Ser Pro Thr Ser Cys Pro Pro Ile Cys Pro Gly Tyr Arg
            20                  25                  30

Trp Met Cys Leu Arg Arg Phe Ile Ile Phe Leu Phe Ile Leu Leu Leu
        35                  40                  45

Cys Leu Ile Phe Leu Leu Val Leu Leu Asp Tyr Gln Gly Met Leu Pro
    50                  55                  60

Val Cys Pro Leu Ile Pro Gly Ser Thr Thr Thr Ser Thr Gly Pro Cys
65                  70                  75                  80

Lys Thr Cys Thr Thr Pro Ala Gln Gly Asn Ser Met Phe Pro Ser Cys
                85                  90                  95

Cys Cys Thr Lys Pro Thr Asp Gly Asn Cys Thr Cys Ile Pro Ile Pro
            100                 105                 110

Ser Ser Trp Ala Phe Ala Lys Tyr Leu Trp Glu Trp Ala Ser Val Arg
        115                 120                 125

Phe Ser Trp Leu Ser Leu Leu Val Pro Phe Val Gln Trp Phe Val Gly
    130                 135                 140

Leu Ser Pro Thr Val Trp Leu Ser Ala Ile Trp Met Met Trp Tyr Trp
145                 150                 155                 160

Gly Pro Ser Leu Tyr Ser Ile Val Ser Pro Phe Ile Pro Leu Leu Pro
                165                 170                 175

Ile Phe Phe Cys Leu Trp Val Tyr Ile
            180                 185

<210> SEQ ID NO 11
<211> LENGTH: 821
<212> TYPE: DNA
<213> ORGANISM: Hepatitis B Virus

<400> SEQUENCE: 11
tctaggggga tctcccgtgt gtcttggcca aaattcgcag tccccaacct ccaatcactc    60
accaacctcc tgtcctccaa tttgtcctgg ttatcgctgg atgtgtctgc ggcgttttat   120
catattcctc ttcatcctgc tgctatgcct catcttctta ttggttcttc tggattatca   180
aggtatgttg cccgtttgtc ctctaattcc aggatcaaca caaccagta cgggaccatg    240 caaaacctgc acgactcctg ctcaaggcaa ctctatgttt ccctcatgtt gctgtacaaa   300
acctacggat ggaaattgca cctgtattcc catcccatcg tcctgggctt cgcaaaata    360 cctatgggag tgggcctcag tccgtttctc atgctcagt ttactagtgc catttgttca   420
gtggttcgta ggacttteec ccactgtttg gctttcagct atgtggatga tgtggtattg   480
ggggccaagt ctgtacagca tcgtgagtcc ctttataccg ctgttaccaa ttttcttttg   540
tctctgggta tacatttaaa ccctaacaaa acaaaaagat ggggttattc cctaaacttc   600
```

```
atgggctaca taattggaag ttggggaact tgccacagg  atcatattgt  acaaaagatc   660
aaacactgtt ttagaaaact tcctgttaac aggcctattg  attggaaagt  atgtcaaaga   720
attgtgggtc ttttgggctt tgctgctcca tttacacaat  gtggatatcc  tgccttaatg   780
cctttgtatg catgtataca agctaaacag gctttcactt  t                       821
```

<210> SEQ ID NO 12
<211> LENGTH: 273
<212> TYPE: PRT
<213> ORGANISM: Hepatitis B Virus

<400> SEQUENCE: 12

```
Ser Arg Gly Ile Ser Arg Val Ser Trp Pro Lys Phe Ala Val Pro Asn
1               5                   10                  15

Leu Gln Ser Leu Thr Asn Leu Leu Ser Ser Asn Leu Ser Trp Leu Ser
            20                  25                  30

Leu Asp Val Ser Ala Ala Phe Tyr His Ile Pro Leu His Pro Ala Ala
        35                  40                  45

Met Pro His Leu Leu Ile Gly Ser Ser Gly Leu Ser Arg Tyr Val Ala
    50                  55                  60

Arg Leu Ser Ser Asn Ser Arg Ile Asn Asn Asn Gln Tyr Gly Thr Met
65                  70                  75                  80

Gln Asn Leu His Asp Ser Cys Ser Arg Gln Leu Tyr Val Ser Leu Met
                85                  90                  95

Leu Leu Tyr Lys Thr Tyr Gly Trp Lys Leu His Leu Tyr Ser His Pro
            100                 105                 110

Ile Val Leu Gly Phe Arg Lys Ile Pro Met Gly Val Gly Leu Ser Pro
        115                 120                 125

Phe Leu Met Ala Gln Phe Thr Ser Ala Ile Cys Ser Val Val Arg Arg
    130                 135                 140

Thr Phe Pro His Cys Leu Ala Phe Ser Tyr Val Asp Asp Val Val Leu
145                 150                 155                 160

Gly Ala Lys Ser Val Gln His Arg Glu Ser Leu Tyr Thr Ala Val Thr
                165                 170                 175

Asn Phe Leu Leu Ser Leu Gly Ile His Leu Asn Pro Asn Lys Thr Lys
            180                 185                 190

Arg Trp Gly Tyr Ser Leu Asn Phe Met Gly Tyr Ile Ile Gly Ser Trp
        195                 200                 205

Gly Thr Leu Pro Gln Asp His Ile Val Gln Lys Ile Lys His Cys Phe
    210                 215                 220

Arg Lys Leu Pro Val Asn Arg Pro Ile Asp Trp Lys Val Cys Gln Arg
225                 230                 235                 240

Ile Val Gly Leu Leu Gly Phe Ala Ala Pro Phe Thr Gln Cys Gly Tyr
                245                 250                 255

Pro Ala Leu Met Pro Leu Tyr Ala Cys Ile Gln Ala Lys Gln Ala Phe
            260                 265                 270

Thr
```

<210> SEQ ID NO 13
<211> LENGTH: 185
<212> TYPE: PRT
<213> ORGANISM: Hepatitis B Virus

<400> SEQUENCE: 13

```
Leu Gly Gly Ser Pro Val Cys Leu Gly Gln Asn Ser Gln Ser Pro Thr
1               5                   10                  15
```

```
Ser Asn His Ser Pro Thr Ser Cys Pro Pro Ile Cys Pro Gly Tyr Arg
         20                  25                  30

Trp Met Cys Leu Arg Arg Phe Ile Ile Phe Leu Phe Ile Leu Leu Leu
         35                  40                  45

Cys Leu Ile Phe Leu Leu Val Leu Leu Asp Tyr Gln Gly Met Leu Pro
 50                  55                  60

Val Cys Pro Leu Ile Pro Gly Ser Thr Thr Thr Ser Thr Gly Pro Cys
 65                  70                  75                  80

Lys Thr Cys Thr Thr Pro Ala Gln Gly Asn Ser Met Phe Pro Ser Cys
                 85                  90                  95

Cys Cys Thr Lys Pro Thr Asp Gly Asn Cys Thr Cys Ile Pro Ile Pro
                100                 105                 110

Ser Ser Trp Ala Phe Ala Lys Tyr Leu Trp Glu Trp Ala Ser Val Arg
         115                 120                 125

Phe Ser Trp Leu Ser Leu Leu Val Pro Phe Val Gln Trp Phe Val Gly
         130                 135                 140

Leu Ser Pro Thr Val Trp Leu Ser Ala Met Trp Met Met Trp Tyr Trp
145                 150                 155                 160

Gly Pro Ser Leu Tyr Ser Ile Val Ser Pro Phe Ile Pro Leu Leu Pro
                165                 170                 175

Ile Phe Phe Cys Leu Trp Val Tyr Ile
                180                 185

<210> SEQ ID NO 14
<211> LENGTH: 686
<212> TYPE: DNA
<213> ORGANISM: Hepatitis B Virus

<400> SEQUENCE: 14 tctagggga  tctcccgtgt  gtcttggcca  aaattcgcag  tccccaacct  ccaatcactc     60
accaacctcc  tgtcctccaa  tttgtcctgg  ttatcgctgg  atgtgtctgc  ggcgttttat    120
catattcctc  ttcatcctgc  tgctatgcct  catcttctta  ttggttcttc  tggattatca    180
aggtatgttg  cccgttttgtc  ctctaattcc  aggatcaaca  acaaccagta  cgggaccatg    240
caaaacctgc  acgactcctg  ctcaaggcaa  ctctatgttt  ccctcatgtt  gctgtacaaa    300
acctacggat  ggaaattgca  cctgtattcc  catcccatcg  tcctgggctt  tcgcaaaata    360
cctatgggat  tgggcctcag  tccgtttctc  atggctcagt  ttactagtgc  catttgttca    420
gtggttcgta  ggactttccc  ccactgtttg  gcttttagct  atgtggatga  tgtggtattg    480
ggggccaagt  ctgtacagca  tcgtgagtcc  ctttataccg  ctgttaccaa  ttttcttttg    540
tctctgggta  tacatttaaa  ccctaacaaa  acaaaaagat  ggggttattc  cctaaacttc    600
atgggttaca  taattggaag  ttggggaaca  ttgccacagg  atcatattgt  acaaaagatc    660
aaacactgtt  ttagaaaact  tcctgt                                            686

<210> SEQ ID NO 15
<211> LENGTH: 228
<212> TYPE: PRT
<213> ORGANISM: Hepatitis B Virus

<400> SEQUENCE: 15

Ser Arg Gly Ile Ser Arg Val Trp Pro Lys Phe Ala Val Pro Asn
 1               5                  10                  15

Leu Gln Ser Leu Thr Asn Leu Leu Ser Ser Asn Leu Ser Trp Leu Ser
         20                  25                  30

Leu Asp Val Ser Ala Ala Phe Tyr His Ile Pro Leu His Pro Ala Ala
```

```
                35                  40                  45
Met Pro His Leu Leu Ile Gly Ser Ser Gly Leu Ser Arg Tyr Val Ala
 50                  55                  60
Arg Leu Ser Ser Asn Ser Arg Ile Asn Asn Gln Tyr Gly Thr Met
 65                  70                  75              80
Gln Asn Leu His Asp Ser Cys Ser Arg Gln Leu Tyr Val Ser Leu Met
                 85                  90                  95
Leu Leu Tyr Lys Thr Tyr Gly Trp Lys Leu His Leu Tyr Ser His Pro
             100                 105                 110
Ile Val Leu Gly Phe Arg Lys Ile Pro Met Gly Leu Gly Leu Ser Pro
             115                 120                 125
Phe Leu Met Ala Gln Phe Thr Ser Ala Ile Cys Ser Val Val Arg Arg
 130                 135                 140
Thr Phe Pro His Cys Leu Ala Phe Ser Tyr Val Asp Asp Val Val Leu
 145                 150                 155                 160
Gly Ala Lys Ser Val Gln His Arg Glu Ser Leu Tyr Thr Ala Val Thr
             165                 170                 175
Asn Phe Leu Leu Ser Leu Gly Ile His Leu Asn Pro Asn Lys Thr Lys
             180                 185                 190
Arg Trp Gly Tyr Ser Leu Asn Phe Met Gly Tyr Ile Ile Gly Ser Trp
 195                 200                 205
Gly Thr Leu Pro Gln Asp His Ile Val Gln Lys Ile Lys His Cys Phe
 210                 215                 220
Arg Lys Leu Pro
 225

<210> SEQ ID NO 16
<211> LENGTH: 185
<212> TYPE: PRT
<213> ORGANISM: Hepatitis B Virus

<400> SEQUENCE: 16

Leu Gly Gly Ser Pro Val Cys Leu Gly Gln Asn Ser Gln Ser Pro Thr
 1               5                  10                  15
Ser Asn His Ser Pro Thr Ser Cys Pro Pro Ile Cys Pro Gly Tyr Arg
                 20                  25                  30
Trp Met Cys Leu Arg Arg Phe Ile Ile Phe Leu Phe Ile Leu Leu Leu
                 35                  40                  45
Cys Leu Ile Phe Leu Leu Val Leu Leu Asp Tyr Gln Gly Met Leu Pro
 50                  55                  60
Val Cys Pro Leu Ile Pro Gly Ser Thr Thr Thr Ser Thr Gly Pro Cys
 65                  70                  75              80
Lys Thr Cys Thr Thr Pro Ala Gln Gly Asn Ser Met Phe Pro Ser Cys
                 85                  90                  95
Cys Cys Thr Lys Pro Thr Asp Gly Asn Cys Thr Cys Ile Pro Ile Pro
             100                 105                 110
Ser Ser Trp Ala Phe Ala Lys Tyr Leu Trp Asp Trp Ala Ser Val Arg
             115                 120                 125
Phe Ser Trp Leu Ser Leu Leu Val Pro Phe Val Gln Trp Phe Val Gly
 130                 135                 140
Leu Ser Pro Thr Val Trp Leu Leu Ala Met Trp Met Met Trp Tyr Trp
 145                 150                 155                 160
Gly Pro Ser Leu Tyr Ser Ile Val Ser Pro Phe Ile Pro Leu Leu Pro
             165                 170                 175

Ile Phe Phe Cys Leu Trp Val Tyr Ile
```

<210> SEQ ID NO 17
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 17
ctttcagcta tgtggatgat gtggtattgg                                    30

<210> SEQ ID NO 18
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 18
ccaataccac atcatccaca tagctgaaag                                    30

<210> SEQ ID NO 19
<211> LENGTH: 29
<212> TYPE: DNA
<213> ORGANISM: Artificial Sequence
<220> FEATURE:
<223> OTHER INFORMATION: oligonucleotide primer

<400> SEQUENCE: 19
tccgtttctc atggctcagt ttactagtg                                     29

<210> SEQ ID NO 20
<211> LENGTH: 29
<212> TYPE: DNA
<213> ORGANISM: Artificial Sequence
<220> FEATURE:
<223> OTHER INFORMATION: oligonucleotide primer

<400> SEQUENCE: 20
cactagtaaa ctgagccatg agaaacgga                                     29

<210> SEQ ID NO 21
<211> LENGTH: 32
<212> TYPE: DNA
<213> ORGANISM: Artificial Sequence
<220> FEATURE:
<223> OTHER INFORMATION: oligonucleotide primer

<400> SEQUENCE: 21
agtggttcgt aggactttcc cccactgttt gg                                 32

<210> SEQ ID NO 22
<211> LENGTH: 33
<212> TYPE: DNA
<213> ORGANISM: Artificial Sequence
<220> FEATURE:
<223> OTHER INFORMATION: oligonucleotide primer

<400> SEQUENCE: 22
agccaaacag tgggggaaag tcctacgaac cac                                33

<210> SEQ ID NO 23
<211> LENGTH: 25
<212> TYPE: DNA
<213> ORGANISM: Artificial Sequence
<220> FEATURE:

```
<223> OTHER INFORMATION: oligonucleotide primer

<400> SEQUENCE: 23
acggggcgca cctctcttta cgcgg                                              25

<210> SEQ ID NO 24
<211> LENGTH: 26
<212> TYPE: DNA
<213> ORGANISM: Artificial Sequence
<220> FEATURE:
<223> OTHER INFORMATION: oligonucleotide primer

<400> SEQUENCE: 24
ctccccgtct gtgccttctc atctgc                                             26

<210> SEQ ID NO 25
<211> LENGTH: 24
<212> TYPE: DNA
<213> ORGANISM: Artificial Sequence
<220> FEATURE:
<223> OTHER INFORMATION: oligonucleotide primer
<221> NAME/KEY: Variant
<222> LOCATION: 13
<223> OTHER INFORMATION: y = t or c

<400> SEQUENCE: 25
gacgtccttt gtytacgtcc cgtc                                               24

<210> SEQ ID NO 26
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 26
tgcagaggtg aagcgaagtg caca                                               24
```